United States Patent
Baran et al.

(10) Patent No.: US 9,526,838 B2
(45) Date of Patent: Dec. 27, 2016

(54) PEN-TYPE INJECTION DEVICE AND ELECTRONIC CLIP-ON MODULE THEREFOR

(71) Applicant: Sanofi-Aventis Deutschland GmbH, Frankfurt am Main (DE)

(72) Inventors: Andre Baran, Steinfurt (DE); Kay Behrendt, Bad Bentheim (DE); Martin Haupt, Vienna (AT)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 14/375,112

(22) PCT Filed: Feb. 8, 2013

(86) PCT No.: PCT/EP2013/052506
§ 371 (c)(1),
(2) Date: Jul. 28, 2014

(87) PCT Pub. No.: WO2013/120774
PCT Pub. Date: Aug. 22, 2013

(65) Prior Publication Data
US 2015/0005713 A1    Jan. 1, 2015

(30) Foreign Application Priority Data

Feb. 13, 2012  (EP) .................................... 12155197
Mar. 27, 2012  (EP) .................................... 12161433

(51) Int. Cl.
*A61M 5/24*        (2006.01)
*G06F 19/00*       (2011.01)
(Continued)

(52) U.S. Cl.
CPC ........... *A61M 5/24* (2013.01); *A61M 5/31525* (2013.01); *F16B 1/00* (2013.01); *F16B 2/02* (2013.01);
(Continued)

(58) Field of Classification Search
CPC ................. A61M 2005/3125; A61M 2205/14; A61M 2205/3306; A61M 2205/502; A61M 2205/582; A61M 2205/6045; A61M 5/24; F16B 17/00; F16B 1/00; F16B 21/06; F16B 7/04
See application file for complete search history.

(56) References Cited

U.S. PATENT DOCUMENTS 6,482,185 B1     11/2002  Hartmann
2010/0286612 A1*  11/2010  Cirillo ............... A61M 5/31525
                                                    604/111
2011/0313349 A1*  12/2011  Krulevitch ............. A61M 5/24
                                                    604/65

FOREIGN PATENT DOCUMENTS

EP     2060284 A1    5/2009
EP     2182456 A1    5/2010
(Continued)

*Primary Examiner* — Kevin C Sirmons
*Assistant Examiner* — Deanna K Hall
(74) *Attorney, Agent, or Firm* — McDonnell Boehnen Hulbert & Berghoff LLP

(57) ABSTRACT

A supplemental device for attachment to an injection device comprises an aligning arrangement for ensuring a predetermined positional relationship between the supplemental device and the injection device; and a securing arrangement for securing the supplemental device to the injection device.

11 Claims, 16 Drawing Sheets

(51) Int. Cl.

| | | |
|---|---|---|
| *F16B 1/00* | (2006.01) | |
| *F16B 2/02* | (2006.01) | |
| *F16B 2/20* | (2006.01) | |
| *F16B 7/04* | (2006.01) | |
| *F16B 21/02* | (2006.01) | |
| *F16B 21/06* | (2006.01) | |
| *A61M 5/315* | (2006.01) | |
| *A61B 5/145* | (2006.01) | |
| *A61M 5/31* | (2006.01) | |

(52) U.S. Cl.
CPC . *F16B 2/20* (2013.01); *F16B 7/04* (2013.01); *F16B 21/02* (2013.01); *F16B 21/06* (2013.01); *G06F 19/3406* (2013.01); *G06F 19/3456* (2013.01); *A61B 5/14532* (2013.01); *A61M 2005/3125* (2013.01); *A61M 2005/3126* (2013.01); *A61M 2205/14* (2013.01); *A61M 2205/18* (2013.01); *A61M 2205/3306* (2013.01); *A61M 2205/3375* (2013.01); *A61M 2205/3592* (2013.01); *A61M 2205/50* (2013.01); *A61M 2205/502* (2013.01); *A61M 2205/52* (2013.01); *A61M 2205/581* (2013.01); *A61M 2205/582* (2013.01); *A61M 2205/6045* (2013.01); *A61M 2205/6072* (2013.01); *A61M 2205/6081* (2013.01); *A61M 2209/04* (2013.01)

(56) References Cited

FOREIGN PATENT DOCUMENTS

| WO | 2009024562 A1 | 2/2009 |
|---|---|---|
| WO | 2010037828 A1 | 4/2010 |
| WO | 2010098927 A1 | 9/2010 |
| WO | 2010128493 A2 | 11/2010 |
| WO | 2011117212 A1 | 9/2011 |

* cited by examiner

PEN-TYPE INJECTION DEVICE AND ELECTRONIC CLIP-ON MODULE THEREFOR

CROSS REFERENCE TO RELATED APPLICATIONS

The present application is a U.S. National Phase application pursuant to 35 U.S.C. §371 of International Application No. PCT/EP2013/052506 filed Feb. 8, 2013, which claims priority to European patent application Ser. No. 12155197.2 filed Feb. 13, 2012, U.S. Provisional Patent Application No. 61/604,699 filed Feb. 29, 2012 and European patent application Ser. No. 12161433.3, filed Mar. 27, 2012. The entire disclosure contents of these applications are herewith incorporated by reference into the present application.

FIELD OF INVENTION

The present invention relates to a supplemental device for attachment to an injection device.

BACKGROUND

A variety of diseases exists that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing an injection button of the insulin pen. To be able to monitor insulin injection, for instance to prevent false handling of the insulin pen or to keep track of the doses already applied, it is desirable to measure information related to a condition and/or use of the injection device, such as for instance information on the injected insulin type and dose. In this respect, WO 2009/024562 discloses a medical device with a value sensor. A Radio Frequency Identification (RFID) unit comprises a value sensor such as a pressure sensor and is integrated with a liquid medicament container to enable wireless pressure or other medicament relevant parameter value monitoring. The liquid medicament container is coupled with a first housing part of the medical device, which first housing part may for instance constitute a pre-filled disposable injection device. The RFID unit communicates wirelessly with a control circuit that is contained in a second housing part of the medical device that is releasably attached to the first housing part. The control circuit is adapted to process the values measured by the RFID unit, to compare it with pre-defined values and to provide an alert to the user if the measured values fall outside normal operating conditions, and to communicate data relating to the measured values to an external device for further data processing.

The control circuit of the medical device described in WO 2009/024562 can thus be used with a series of pre-filled disposable injection devices, but the requirement that the RFID unit with the value sensor is contained in the medicament container of the pre-filled disposable injection devices significantly increases the costs of the pre-filled disposable injection device.

It has been described, for instance in WO 2011/117212 to provide a supplementary device comprising a mating unit for releasably attaching the device to an injection device. The device includes a camera and is configured to perform optical character recognition (OCR) on captured images visible through a dosage window of the injection pen, thereby to determine a dose of medicament that has been dialed into the injection device.

SUMMARY

According to a first aspect of the present invention, there is provided a supplemental device for attachment to an injection device, the supplemental device comprising:

an aligning arrangement for ensuring a predetermined positional relationship between the supplemental device and the injection device; and a securing arrangement for securing the supplemental device to the injection device.

The aligning arrangement and the securing arrangement may be separate arrangements.

The aligning arrangement may comprise a locating channel in a main body of the supplemental device, the locating channel being configured to mate with a locating rib on the injection device. Here, the locating channel may be located at one end of the main body of the supplemental device.

The aligning arrangement may comprise first and second protuberances located on first and second support members respectively, and the supplemental device may be configured such that the protuberances engage in indents on the injection device when the predetermined positional relationship is present. Here, the supplemental device has a main body defining an injection device receiving channel, the protuberances may be located one either side of the injection device receiving channel, and the support members may be biased towards each other. Here, the protuberances may have sloping sides, and a gradient of a side of each protuberance that is closest to the bottom of the injection device receiving channel may be greater than a gradient of a side of the protuberance that is furthest from the bottom of the injection device receiving channel.

The supplemental device may include an optical reading arrangement and the optical reading arrangement may be directed at and at least partially covers a display of the injection device when the predetermined positional relationship between the supplemental device and the injection device is present.

The supplemental device may have a main body defining an injection device receiving channel, and the securing arrangement may comprise a closure that is removably attachable across the injection device receiving channel.

The securing arrangement may be movably attached to the main body at a first side of the injection device receiving channel. Here, the securing arrangement may be hinged to the main body at a first side of the injection device receiving channel.

The securing arrangement may be removably connectable to the main body of the supplemental device at a second side of the injection device receiving channel by a latch and catch arrangement.

The aligning arrangement and the securing arrangement may comprise parts that contribute to both alignment and securing of the supplemental device on/to the injection device.

The aligning arrangement may comprise at least one protuberance, and the supplemental device may be configured such that the at least one protuberance engages in an indent on the injection device when the predetermined positional relationship is present. The at least one protuberance may be located on a support member.

In one embodiment the aligning arrangement may comprise first and second protuberances, and the supplemental device may be configured such that the first and second protuberances engage in respective indents on the injection device when the predetermined positional relationship is present. The first and second protuberance may be located on a first and second support member, respectively.

The first and second support members may be biased towards each other. In addition the first and second support members may be releasably forced towards each other, e.g. by a closure. When such a securing force is present, the supplemental device is secured to the injection device. The supplemental device may then still remain attached to the injection device due to the biasing force of the support members.

The securing arrangement may comprise at least one protuberance, and the supplemental device may be configured such that the at least one protuberance engages in an indent on the injection device when the predetermined positional relationship is present. The at least one protuberance may be located on a closure or a hinged securing arrangement.

The securing arrangement may comprise at least one flexible support member and/or at least one hinged securing arrangement. For example, the supplemental device may comprise two flexible support members and a hinged closure.

A second aspect of the invention provides a system comprising a supplemental device as above and an injection device.

The supplemental device may be located so as not to inhibit user access to a dosage knob or an injection button of the injection device when the predetermined positional relationship between the supplemental device and the injection device is present.

The supplemental device may be located so as not to fully cover a medicament information label provided on the injection device when the predetermined positional relationship between the supplemental device and the injection device is present.

The supplemental device may be located so as to at least partly cover a dose window or display of the injection device when the predetermined positional relationship between the supplemental device and the injection device is present.

The injection device may comprise at least one protrusion interacting with the aligning arrangement of the supplemental device. The at least one protrusion may comprise a locating rib.

The injection device may comprise at least one indent interacting with the alignment arrangement of the supplemental device.

The injection device may comprise a locating rib and two indents which are in engagement with a locating channel and protuberances, respectively, of the supplemental device.

A third aspect of the invention provides the use of at least one protrusion and/or at least one indent on an injection device for aligning and/or securing a supplemental device on the injection device by interacting with an aligning arrangement and/or a securing arrangement of the supplemental device. The at least one protrusion and/or at least one indent on an injection device may be used for aligning or securing a supplemental device on the injection device by interacting with an aligning arrangement and/or a securing arrangement of the supplemental device. The at least one protrusion and/or at least one indent on an injection device may be used for aligning and securing a supplemental device on the injection device by interacting with an aligning arrangement and/or a securing arrangement of the supplemental device.

The protrusion on the injection device may be a locating rib interacting with a locating channel of the supplemental device. The protrusion on the injection device may, however, have any shape suitable to interact with a locating channel of the supplemental device. The protrusion may, e.g., comprise a pip, nose, bump, or the like structure.

The injection device may comprise two indents interacting with two protuberances of the supplemental device. The indents may, e.g., comprise holes, dents, slots, groves, steps Embodiments of the invention will now be described, by way of example only, with reference to the accompanying drawings.

BRIEF DESCRIPTION OF THE DRAWINGS

The figures show:

FIG. 1b shows a perspective view of some detail of the injection device of FIG. 1a;

FIG. 4: a schematic view of the supplementary device of FIG. 2a in a state where it is attached to the injection device of FIG. 1a;

FIG. 8 (shown on two sheets FIG. 8a and FIG. 8b) is a side view of the supplemental device of FIG. 2b attached to the injection pen of FIG. 1a;

DETAILED DESCRIPTION

In the following, embodiments of the present invention will be described with reference to an insulin injection device. The present invention is however not limited to such application and may equally well be deployed with injection devices that eject other medicaments, or with other types of medical devices.

Figure 1A:
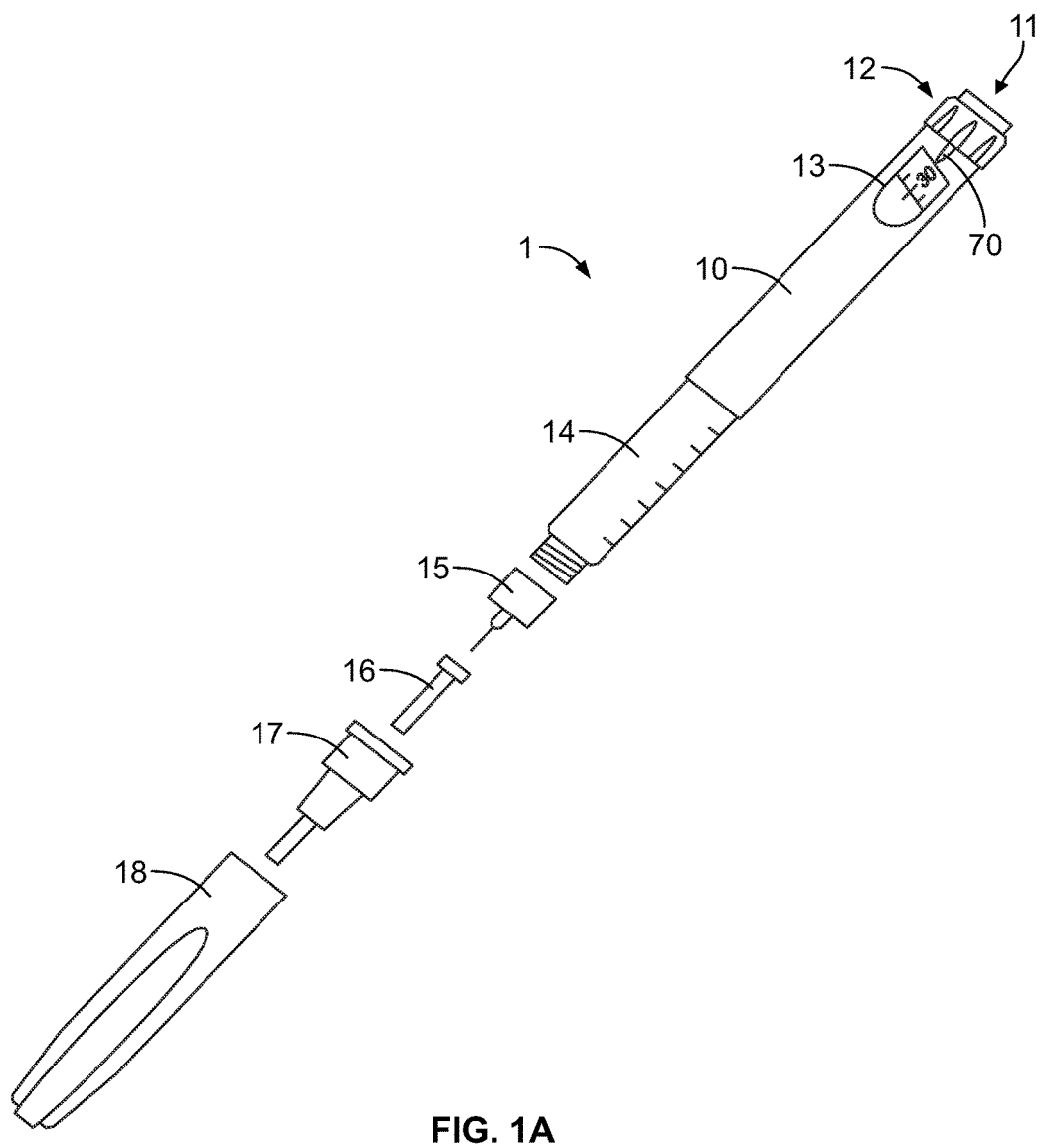
FIG. 1a: an exploded view of an injection device.

FIG. 1a is an exploded view of an injection device 1, which may for instance represent Sanofi's Solostar (R) insulin injection pen.

The injection device 1 of FIG. 1a is a pre-filled, disposable injection pen that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1a. It should be noted that the selected dose may equally well be displayed differently, for instance by an electronic display. A label (not shown) is provided on the housing 10. The label includes information about the medicament included within the injection device, including information identifying the medicament. The information identifying the medicament may be in the form of text. The information identifying the medicament may also be in the form of a colour. The information identifying the medicament may also be encoded into a barcode, QR code or the like. The information identifying the medicament may also be in the form of a black and white pattern, a colour pattern or shading.

Turning the dosage knob 12 causes a mechanical click sound to provide acoustical feedback to a user. The numbers displayed in dosage window 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Injection device 1 may be used for several injection processes until either insulin container 14 is empty or the expiration date of injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 1B:
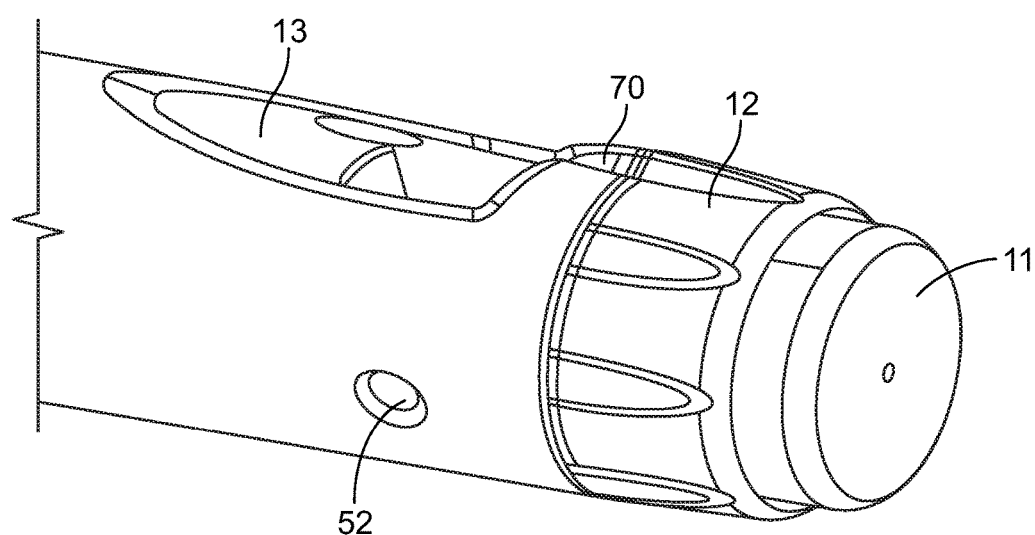

FIG. 1b is a close-up of the end of the injection device 1. This FIG. shows a locating rib 70 that is located between the viewing window 13 and the dosage knob 12.

Figure 2A:
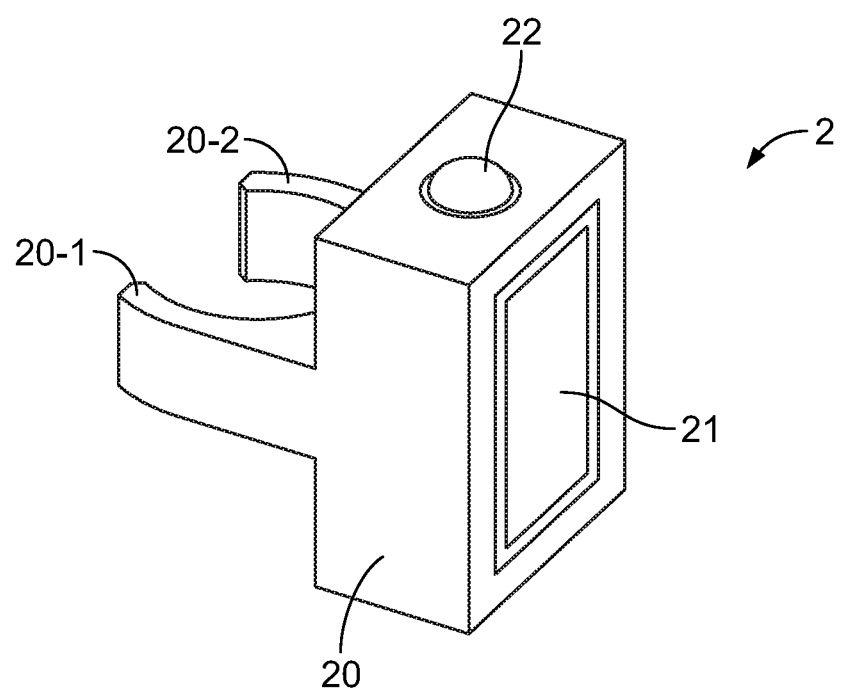
FIG. 2a: a schematic illustration of a supplementary device to be releasably attached to the injection device of FIG. 1a according to an embodiment of the present invention.

FIG. 2a is a schematic illustration of an embodiment of a supplementary device 2 to be releasably attached to injection device 1 of FIG. 1a. Supplementary device 2 comprises a housing 20 with a mating unit configured and embrace the housing 10 of injection device 1 of FIG. 1a, so that supplementary device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplementary device 2 contains optical and acoustical sensors for gathering information from injection device 1. At least a part of this information, for instance a selected dose (and optionally a unit of this dose), is displayed via display unit 21 of supplementary device 2. The dosage window 13 of injection device 1 is obstructed by supplementary device 2 when attached to injection device 1.

Supplementary device 2 further comprises three user input transducers, illustrated schematically as a button 22. These input transducers 22 allow a user to turn on/off supplementary device 2, to trigger actions (for instance to cause establishment of a connection to or a pairing with another device, and/or to trigger transmission of information from supplementary device 2 to another device), or to confirm something.

Figure 2B:
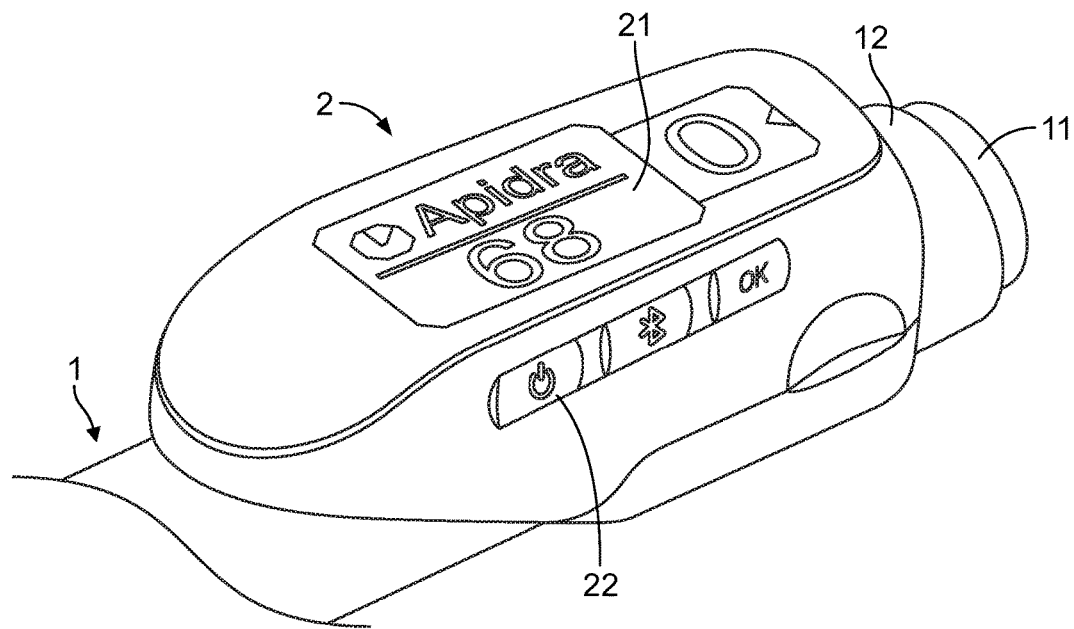
FIG. 2b: a perspective view of a supplementary device to be releasably attached to the injection device of FIG. 1a according to various embodiments of the present invention.

FIG. 2b is a schematic illustration of a second embodiment of a supplementary device 2 to be releasably attached to injection device 1 of FIG. 1a. Supplementary device 2 comprises a housing 20 with a mating unit configured and embrace the housing 10 of injection device 1 of FIG. 1a, so that supplementary device 2 sits tightly on housing 10 of injection device 1, but is nevertheless removable from injection device 1.

Information is displayed via display unit 21 of supplementary device 2. The dosage window 13 of injection device 1 is obstructed by supplementary device 2 when attached to injection device 1.

Supplementary device 2 further comprises three user input buttons or switches. A first button 22 is a power on/off button, via which the supplementary device 2 may for instance be turned on and off. A second button 33 is a communications button. A third button 34 is a confirm or OK button. The buttons 22, 33, 34 may be any suitable form of mechanical switch. These input buttons 22, 33, 34 allow a user to turn on/off supplementary device 2, to trigger actions (for instance to cause establishment of a connection to or a pairing with another device, and/or to trigger transmission of information from supplementary device 2 to another device), or to confirm something.

Figure 2C:
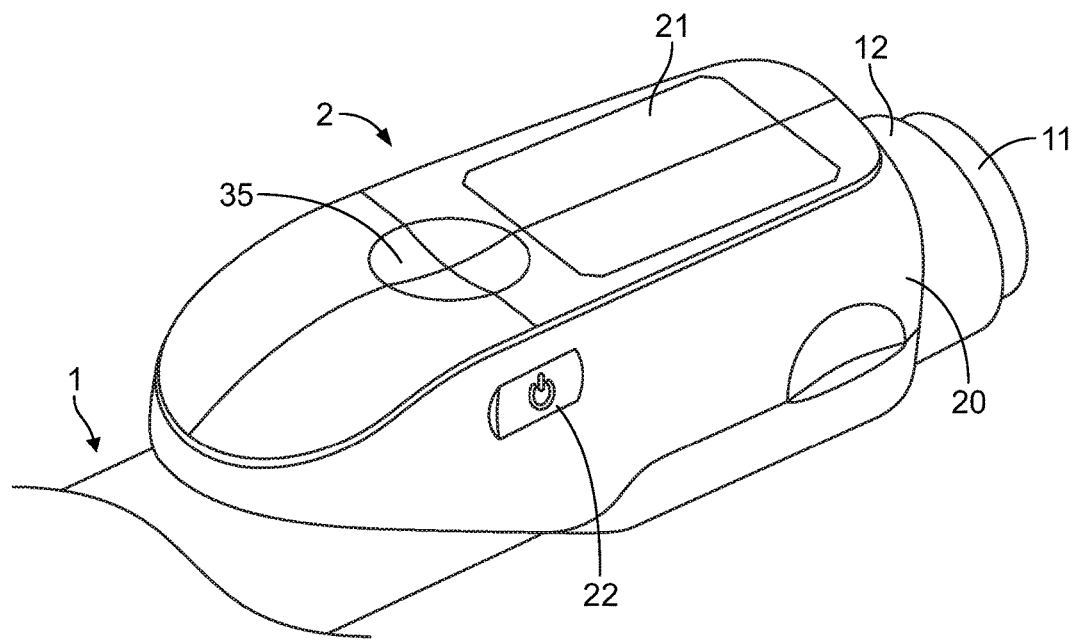
FIG. 2c: a perspective view of a supplementary device to be releasably attached to the injection device of FIG. 1a according to other embodiments of the present invention.

FIG. 2c is a schematic illustration of a third embodiment of a supplementary device 2 to be releasably attached to injection device 1 of FIG. 1a. Supplementary device 2 comprises a housing 20 with a mating unit configured and embrace the housing 10 of injection device 1 of FIG. 1a, so that supplementary device 2 sits tightly on housing 10 of injection device 1, but is nevertheless removable from injection device 1.

Information is displayed via display unit 21 of the supplementary device 2. The dosage window 13 of injection device 1 is obstructed by supplementary device 2 when attached to injection device 1.

Supplementary device 2 further comprises a touch-sensitive input transducer 35. It also comprises a single user input button or switch 22. The button 22 is a power on/off button, via which the supplementary device 2 may for instance be turned on and off. The touch sensitive input transducer 35 can be used to trigger actions (for instance to cause establishment of a connection to or a pairing with another device, and/or to trigger transmission of information from supplementary device 2 to another device), or to confirm something.

Figure 3A:
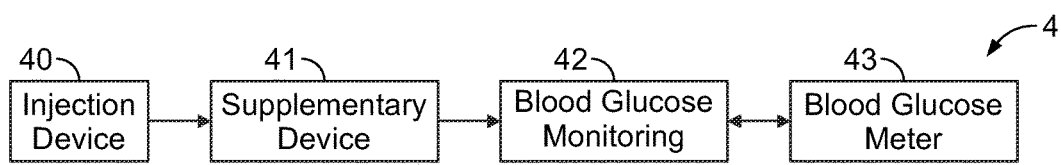
FIGS. 3A and 3b: possible distributions of functions among devices when using a supplementary device (such as the supplementary devices of FIGS. 2a and 2b) together with an injection device.
Figure 3B:
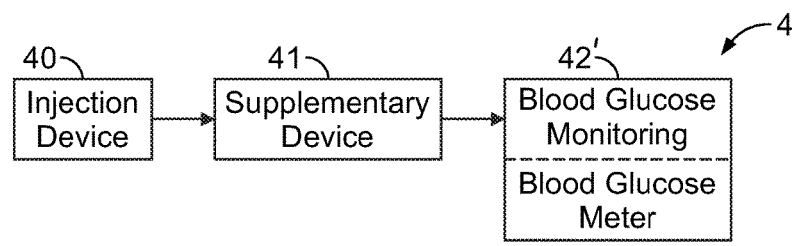

FIGS. 3A and 3b show possible distributions of functions among devices when using a supplementary device (such as the supplementary devices of FIGS. 2a and 2b) together with an injection device.

In constellation 4 of FIG. 3a, the supplementary device 41 (such as the supplementary devices of FIGS. 2a and 2b) determines information from injection device 40, and provides this information (e.g. type and/or dose of the medicament to be injected) to a blood glucose monitoring system 42 (e.g. via a wired or wireless connection).

Blood glucose monitoring system 42 (which may for instance be embodied as desktop computer, personal digital assistant, mobile phone, tablet computer, notebook, netbook or ultrabook) keeps a record of the injections a patient has received so far (based on the ejected doses, for instance by assuming that the ejected doses and the injected doses are the same, or by determining the injected doses based on the ejected doses, for instance be assuming that a pre-defined percentage of the ejected dose is not completely received by the patient). Blood glucose monitoring system 42 may for instance propose a type and/or dose of insulin for the next injection for this patient. This proposal may be based on information on one or more past injections received by the patient, and on a current blood glucose level, that is measured by blood glucose meter 43 and provided (e.g. via a wired or wireless connection) to blood glucose monitoring system 42. Therein, blood glucose meter 43 may be embodied as a separate device that is configured to receive a small blood probe (for instance on a carrier material) of a patient and to determine the blood glucose level of the patient based on this blood probe. Blood glucose meter 43 may however also be a device that is at least temporarily implanted into the patient, for instance in the patient's eye or beneath the skin.

FIG. 3b is a modified constellation 4' where the blood glucose meter 43 of FIG. 3a has been included into blood glucose monitoring system 42 of FIG. 3a, thus yielding the modified blood glucose monitoring system 42' of FIG. 3b. The functionalities of injection device 40 and supplementary device 41 of FIG. 3a are not affected by this modification.

Also the functionality of blood glucose monitoring system 42 and blood glucose meter 43 combined into blood glucose monitoring system 42' are basically unchanged, apart from the fact that both are now comprised in the same device, so that external wired or wireless communication between these devices is no longer necessary. However, communication between blood glucose monitoring system 42 and blood glucose meter 43 takes place within system 42'.

Figure 4:
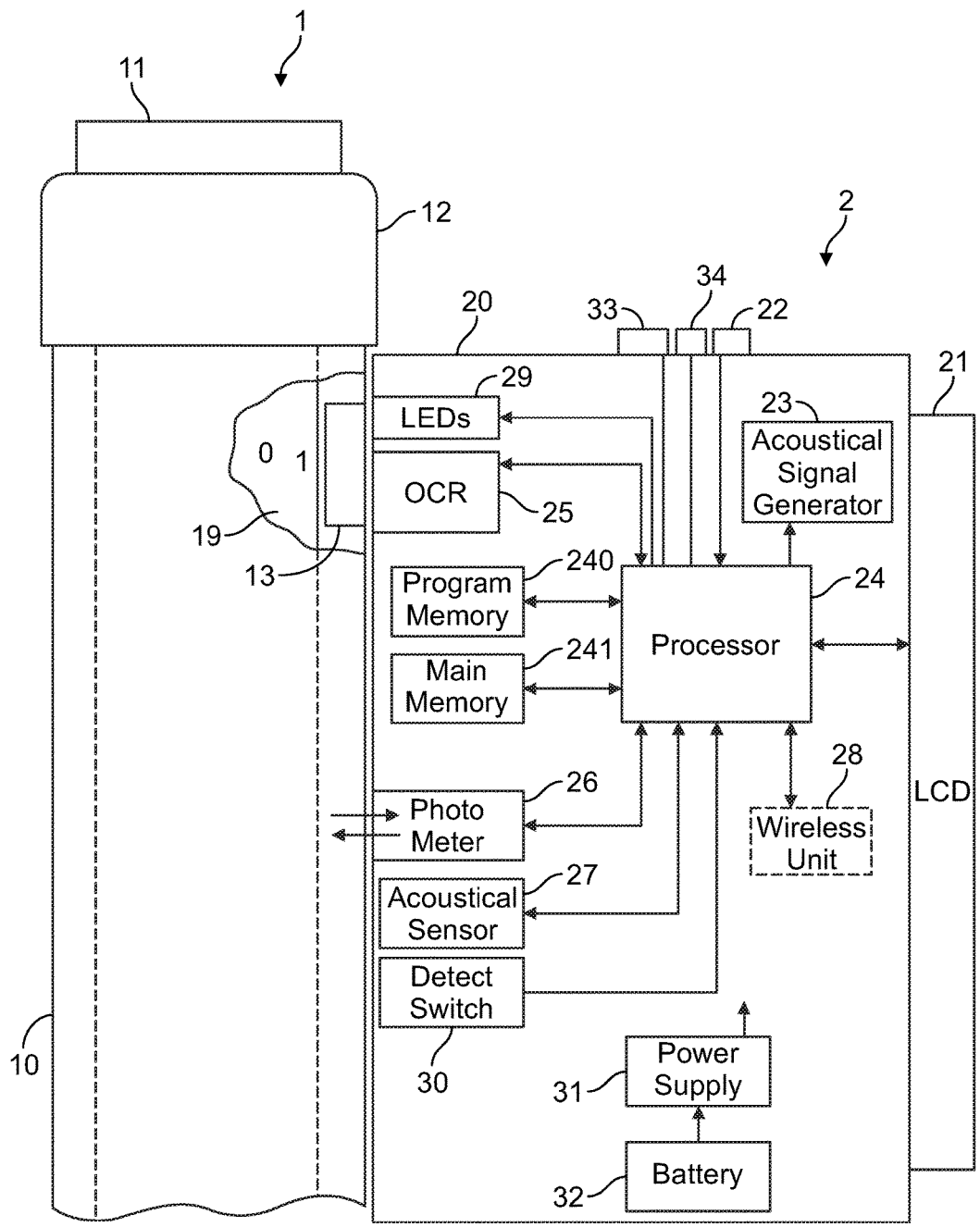

FIG. 4 shows a schematic view of the supplementary device 2 of FIG. 2a in a state where it is attached to injection device 1 of FIG. 1a.

With the housing 20 of supplementary device 2, a plurality of components are comprised. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. Main memory 241 may also be used to store a logbook on performed ejections/injections. Program memory 240 may for instance be a Read-Only Memory (ROM), and main memory may for instance be a Random Access Memory (RAM).

In embodiments such as those shown in FIG. 2b, processor 24 interacts with a first button 22, via which supplementary device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplementary device 2. In embodiments such as those shown in FIG. 2c, two of the buttons 33, 34 may be omitted. Instead, one or more capacitive sensors or other touch sensors are provided.

Processor 24 controls a display unit 21, which is presently embodied as a Liquid Crystal Display (LCD). Display unit 21 is used to display information to a user of supplementary device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage window 13, in which a currently selected dose is displayed (by way of numbers printed on the sleeve 19 contained in injection device 1, which numbers are visible through the dosage window 13). OCR reader 25 is further capable of recognizing characters (e.g. numbers) from the captured image and to provide this information to processor 24. Alternatively, unit 25 in supplementary device 2 may only be an optical sensor, e.g. a camera, for capturing images and providing information on the captured images to processor 24. Then processor 24 is responsible for performing OCR on the captured images.

The numbers shown on a display window 13 of injection device 1 could comprise odd and/or even numbers.

The processor is capable of transforming the information from the captured image into information to be indicated on the display unit 21 of the supplementary device 2. The information indicated on the display unit 21 could be a representation or reproduction of the image or image information. The information indicated on the display unit 21 could be an interpretation of the image or image information.

For example, the display window 13 of injection device 1 may show the numbers "12" and "14" centered which corresponds to a dose of "13 units". The processor could control the display to indicate a representation or reproduction of the image, i.e. the display could indicate the numbers "12" and "14".

The processor 24 may be capable of interpreting the image information and transform it into information to be indicated on the display unit 21. Taking the above example, the image processor 24 may be capable of interpreting the image information as to correspond to a dose of "13 units" and transform the information accordingly. Processor 24 would control the display unit 21 to indicate an interpretation of the image. The display unit 21 could for example indicate "13" or "13 units".

Processor 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens (e.g. an aspheric lens) leading to a magnification (e.g. a magnification of more than 3:1).

Processor 24 further controls a photometer 26, that is configured to determine an optical property of the housing 10 of injection device 1, for example a colour or a shading. The optical property may only be present in a specific portion of housing 10, for example a colour or colour coding of sleeve 19 or of an insulin container comprised within injection device 1, which colour or colour coding may for instance be visible through a further window in housing 10 (and/or in sleeve 19). Information on this colour is then provided to processor 24, which may then determine the type of injection device 1 or the type of insulin contained in injection device 1 (e.g. SoloStar Lantus with purple colour and SoloStar Apidra with blue colour). Alternatively, a camera unit may be used instead of photometer 26, and an image of the housing, sleeve or insulin container may then be provided to processor 24 to determine the colour of the housing, sleeve or insulin container by way of image processing. Further, one or more light sources may be provided to improve reading of photometer 26. The light source may provide light of a certain wavelength or spectrum to improve colour detection by photometer 26. The light source may be arranged in such a way that unwanted reflections, for example by dosage window 13, are avoided or reduced. In an example embodiment, instead of or in addition to photometer 26, a camera unit may be deployed to detect a code (for instance a bar code, which may for instance be a one- or two-dimensional bar code) related to the injection device and/or the medicament contained therein. This code may for instance be located on the housing 10 or on a medicament container contained in injection device 1, to name but a few examples. This code may for instance indicate a type of the injection device and/or the medicament, and/or further properties (for instance a expiration date).

Processor 24 further controls (and/or receives signals from) an acoustic sensor 27, which is configured to sense sounds produced by injection device 1. Such sounds may for instance occur when a dose is dialed by turning dosage knob 12 and/or when a dose is ejected/injected by pressing injection button 11, and/or when a prime shot is performed. These actions are mechanically similar but nevertheless sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 further controls an acoustical signal generator 23, which is configured to produce acoustical signals that may for instance be related to the operating status of injection device 1, for instance as feedback to the user. For example, an acoustical signal may be launched by acoustical signal generator 23 as a reminder for the next dose to be injected or as a warning signal, for instance in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 controls a wireless unit 28, which is configured to transmit and/or receive information to/from another device in a wireless fashion. Such transmission may for instance be based on radio transmission or optical transmission. In some embodiments, the wireless unit 28 is a Bluetooth transceiver. Alternatively, wireless unit 28 may be substituted or complemented by a wired unit configured to transmit and/or receive information to/from another device in a wire-bound fashion, for instance via a cable or fibre connection. When data is transmitted, the units of the data (values) transferred may be explicitly or implicitly defined. For instance, in case of an insulin dose, always International Units (IU) may be used, or otherwise, the used unit may be transferred explicitly, for instance in coded form.

Processor 24 receives an input from a pen detection switch 30, which is operable to detect whether the pen 1 is present, i.e. to detect whether the supplementary device 2 is coupled to the injection device 1.

A battery 32 powers the processor 24 and other components by way of a power supply 31.

The supplementary device 2 of FIG. 4 is thus capable of determining information related to a condition and/or use of injection device 1. This information is displayed on the display 21 for use by the user of the device. The information may be either processed by supplementary device 2 itself, or may at least partially be provided to another device (e.g. a blood glucose monitoring system).

Figure 5A:
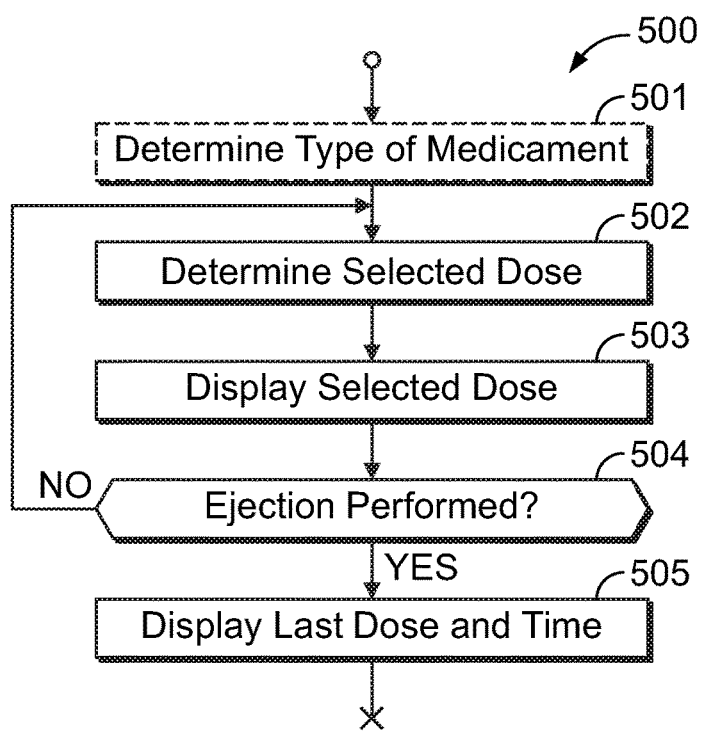
FIG. 5a: a flowchart of a method used in various embodiments.
Figure 5B:
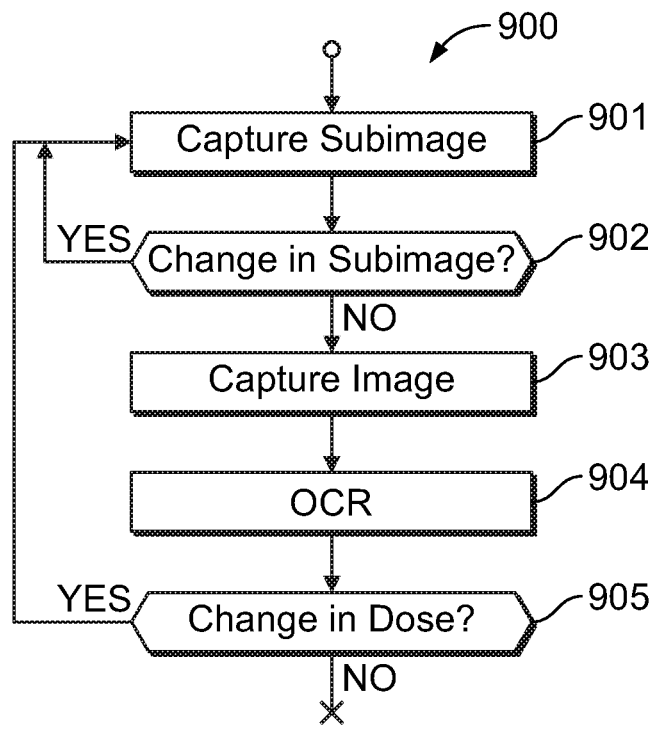
FIG. 5b: a flowchart of a further method used in various embodiments.
Figure 5C:
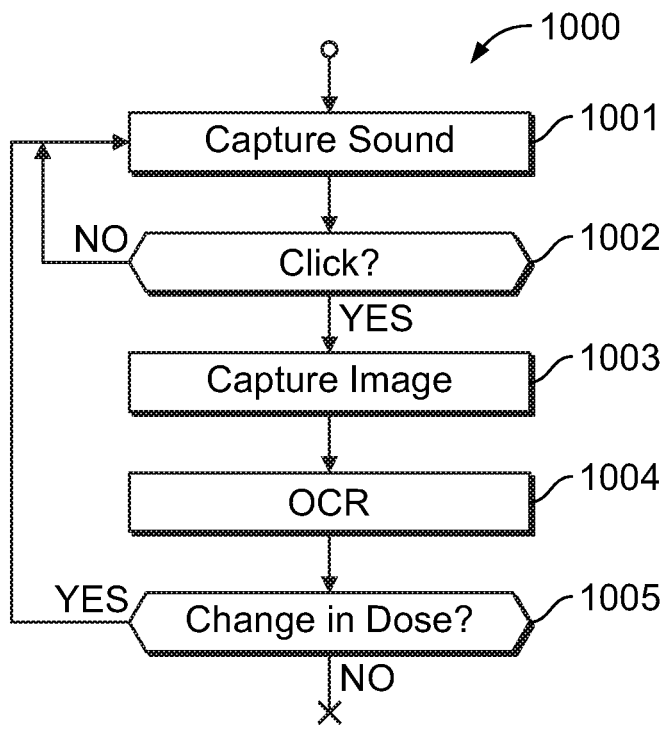
FIG. 5c: a flowchart of a still further method used in various embodiments.

FIGS. 5a-5c are flowcharts of embodiments of methods according to the present invention. These methods may for instance be performed by processor 24 of supplementary device 2 (see FIGS. 2b and 4), but also by a processor of supplementary device 3 of FIG. 2b, and may for instance be stored in program memory 240 of supplementary device 2, which may for instance take the shape of tangible storage medium 60 of FIG. 6.

FIG. 5a shows method steps that are performed in scenarios as shown in FIGS. 3a and 3b, where information read by supplementary device 41 from injection device 40 is provided to blood glucose monitoring system 42 or 42' without receiving information back from blood glucose monitoring system 42 or 42'.

The flowchart 500 starts for instance when the supplementary device is turned on or is otherwise activated. In a step 501, a type of medicament, for example insulin, provided by the injection device is determined, for instance based on colour recognition or based on recognition of a code printed on injection device or a component thereof as already described above. Detection of the type of medicament may not be necessary if a patient always takes the same type of medicament and only uses an injection device with this single type of medicament. Furthermore, determination of the type of medicament may be ensured otherwise (e.g. by the key-recess pair shown in FIG. 4 that the supplementary device is only useable with one specific injection device, which may then only provide this single type of medicament).

In a step 502, a currently selected dose is determined, for instance by OCR of information shown on a dosage window of injection device as described above. This information is then displayed to a user of the injection device in a step 503.

In a step 504, it is checked if an ejection has taken place, for instance by sound recognition as described above. Therein, a prime shot may be differentiated from an actual injection (into a creature) either based on respectively different sounds produced by the injection device and/or based on the ejected dose (e.g. a small dose, for instance less than a pre-defined amount of units, e.g. 4 or 3 units, may be considered to belong to a prime shot, whereas larger doses are considered to belong to an actual injection).

If an ejection has taken place, the determined data, i.e. the selected dose and—if applicable—the type of medicament (e.g. insulin), is stored in the main memory 241, from where it may later be transmitted to another device, for instance a blood glucose monitoring system. If a differentiation has been made concerning the nature of the ejection, for instance if the ejection was performed as a prime shot or as an actual injection, this information may also be stored in the main memory 241, and possibly later transmitted. In the case of an injection having been performed, at step 505 the dose is displayed on the display 21. Also displayed is a time since the last injection which, immediately after injection, is 0 or 1 minute. The time since last dose may be displayed intermittently. For instance, it may be displayed alternately with the name or other identification of the medicament that was injected, e.g. Apidra or Lantus.

If ejection was not performed at step 504, steps 502 and 503 are repeated.

After display of the delivered dose and time data, the flowchart 500 terminates.

FIG. 5b shows in more detail exemplary method steps that are performed when the selected dose is determined based on the use of optical sensors only. For instance, these steps may be performed in step 502 of FIG. 5a.

In a step 901, a sub-image is captured by an optical sensor such as optical sensor 25 of supplementary device 2. The captured sub-image is for instance an image of at least a part of the dosage window 13 of injection device 1, in which a currently selected dose is displayed (e.g. by way of numbers and/or a scale printed on the sleeve 19 of injection device 1, which is visible through the dosage window 13). For instance, the captured sub-image may have a low resolution and/or only show a part of the part of sleeve 19 which is visible through dosage window 13. For instance, the captured sub-image either shows the numbers or the scale printed on the part of sleeve 19 of injection device 1 which is visible through dosage window 13. After capturing an image, it is, for instance, further processed as follows:

Division by a previously captured background image;
Binning of the image(s) to reduce the number of pixels for further evaluations;
Normalization of the image(s) to reduce intensity variations in the illumination;
Sheering of the image(s); and/or
Binarization of the image(s) by comparing to a fixed threshold.

Several or all of these steps may be omitted if applicable, for instance if a sufficiently large optical sensor (e.g. a sensor with sufficiently large pixels) is used.

In a step 902, it is determined whether or not there is a change in the captured sub-image. For instance, the currently captured sub-image may be compared to the previously captured sub-image(s) in order to determine whether or not there is a change. Therein, the comparison to previously captured sub-images may be limited to the sub-image of the previously captured sub-images that was captured immediately before the current sub-image was captured and/or to the sub-images of the previously captured sub-images that were captured within a specified period of time (e.g. 0.1 seconds) before the current sub-image was captured. The comparison may be based on image analysis techniques such as pattern recognition performed on the currently captured sub-image and on the previously captured sub-image. For instance, it may be analyzed whether the pattern of the scale and/or the numbers visible through the dosage window 13 and shown in the currently captured sub-image and in the previously captured sub-image is changed. For instance, it may be searched for patterns in the image that have a certain size and/or aspect ratio and these patterns may be compared with previously saved patterns. Steps 901 and 902 may correspond to a detection of a change in the captured image.

If it is determined in step 902 that there is a change in the sub-image, step 901 is repeated. Otherwise in a step 903, an image is captured by an optical sensor such as optical sensor 25 of supplementary device 2. The captured image is for instance an image of the dosage window 13 of injection device 1, in which a currently selected dose is displayed (e.g. by way of numbers and/or a scale printed on the sleeve 19 of injection device 1, which is visible through the dosage window 13). For instance, the captured image may have a resolution being higher than the resolution of the captured sub-image. The captured image at least shows the numbers printed on the sleeve 19 of injection device 1 which are visible through the dosage window 13.

In a step 904, optical character recognition (OCR) is performed on the image captured in step 903 in order to recognize the numbers printed on the sleeve 19 of injection device 1 and visible through the dosage window 13, because these numbers correspond to the (currently) selected dose. In accord to the recognized numbers, the selected dose is determined, for instance by setting a value representing the selected dose to the recognized numbers.

In a step 905, it is determined whether or not there is a change in the determined selected dose and, optionally, whether or not the determined selected dose does not equal zero. For instance, the currently determined selected dose may be compared to the previously determined selected dose(s) in order to determine whether or not there is a change. Therein, the comparison to previously determined selected dose(s) may be limited to the previously determined selected dose(s) that were determined within a specified period of time (e.g. 3 seconds) before the current selected dose was determined. If there is no change in the determined selected dose and, optionally, the determined selected dose does not equal zero, the currently determined selected dose is returned/forwarded for further processing (e.g. to processor 24).

Thus, the selected dose is determined if the last turn of the dosage knob 12 is more than 3 seconds ago. If the dosage knob 12 is turned within or after these 3 seconds and the new position remains unchanged for more than 3 seconds, this value is taken as the determined selected dose.

FIG. 5c shows in more detail method steps that are performed when the selected dose is determined based on the use of acoustical and optical sensors. For instance, these steps may be performed in step 502 of FIG. 5*a*.

In a step 1001, a sound is captured by an acoustical sensor such as acoustical sensor 27 of supplementary device 2.

In a step 1002, it is determined whether or not the captured sound is a click sound. The captured sound may for instance be a click sound that occurs when a dose is dialed by turning dosage knob 12 of injection device 1 and/or when a dose is ejected/injected by pressing injection button 11, and/or when a prime shot is performed. If the captured sound is not a click sound, step 1001 is repeated. Otherwise in a step 1003, an image is captured by an optical sensor such as optical sensor 25 of supplementary device 2. Step 1003 corresponds to step 903 of flowchart 900.

In a step 1004, an OCR is performed on the image captured in step 1003. Step 1004 corresponds to step 904 of flowchart 900.

In a step 1005, it is determined whether or not there is a change in the determined selected dose and, optionally, whether or not the determined selected dose does not equal zero. Step 1005 corresponds to step 905 of flowchart 900.

There might be a slight advantage of the acoustic approach shown in FIG. 5*c* when it comes to power consumption of the supplementary device, because permanently capturing images or sub-images as shown in FIG. 5*b* typically is more power consuming than listening to an acoustical sensor such as a microphone.

Figure 6:
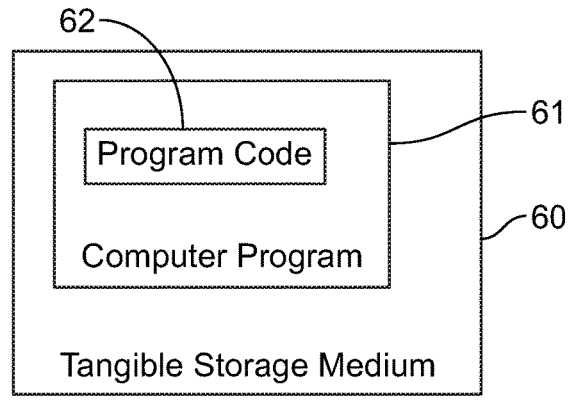
FIG. 6: a schematic illustration of a tangible storage medium 60 according to an embodiment of the present invention.
Figure 7:
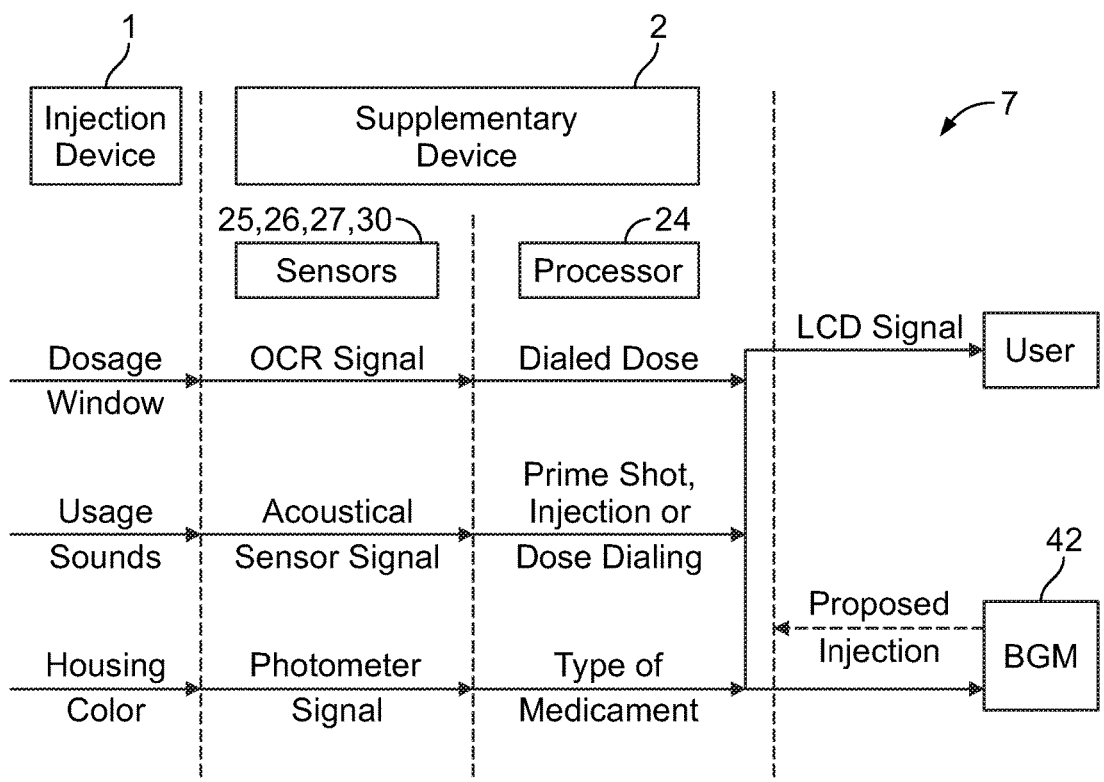
FIG. 7: an information sequence chart that illustrates an information flow between various devices according to embodiments of the invention.

FIG. 6 is a schematic illustration of a tangible storage medium 600 (a computer program product) that comprises a computer program 601 with program code 602. This program code may for instance be executed by processors contained in the supplementary device, for instance processor 24 of supplementary device 2 of FIGS. 2 and 4. For instance, storage medium 600 may represent program memory 240 of supplementary device 2 of FIG. 4. Storage medium 600 may be a fixed memory, or a removable memory, such as for instance a memory stick or card.

As described in detail above, embodiments of the present invention allow connection of a standard injection device, in particular an insulin device, with a blood glucose monitoring system in a useful and productive way.

Embodiments of the present invention introduce a supplementary device to allow for this connection, assuming the blood glucose monitoring system has wireless or other communication capabilities.

The benefits from the connection between the blood glucose monitoring and an insulin injection device are inter alia the reduction of mistakes by the user of the injection device and a reduction of handling steps—no more manual transfer of the injected insulin unit to a blood glucose monitoring is required, in particular to a blood glucose monitoring system with functionality of providing guidance for the next dose based on the last dose injected and latest blood glucose values.

As described with reference to exemplary embodiments above, when a user/patient gets a new insulin pen, the user attaches the supplementary device to the pen. The supplementary device reads out the injected dose. It may also transfer it to a blood glucose monitoring system with insulin titration capabilities. For patients taking multiple insulins, the supplementary device recognizes the device structure to the insulin type and may also transmit this piece of information to the blood glucose monitoring system.

In example embodiments, the information shown on a display, for example LCD display 21 of FIGS. 2*a* and 4, may also converted to a sound signal played to a user through a speaker, for example by a text-to-speech functionality implemented by processor 24 using the acoustical signal generator 23. Thus, a user with impaired vision may have improved access to the information of supplementary device 2, such as a dialed dose, a recommended dose, a recommended time for administration and/or the like.

When using embodiments of the present invention, the user inter alia has the following advantages:

The user can use the most convenient disposable insulin injector.

The supplementary device is attachable and detachable (reusable).

The user may still use the injection device in the same way in which he is used to using it. This is in spite of the fact that the display window 13 is covered by the supplemental device.

The user can identify that the injection device is the correct one to use, particularly he can check that it contains the correct medicament. This is in spite of the fact that a medicament information label of the injection device is partly covered by the supplemental device.

Injected dose information may be transferred to the blood glucose monitoring system automatically (no more transfer mistakes). Improved dose guidance may result from this as the blood glucose monitoring system calculates the dose to be taken.

Keeping of a manual data logbook may not be needed any more.

Furthermore, when deploying the supplementary device proposed by the present invention, patients may also be reminded of injecting their next dose by receiving an alarm signal, for instance, after an appropriate time after a first dose of a medicament (for instance insulin or heparin) has been injected.

Injected dose information may be transferred to any computerized system, for instance as input for any dose calculation or any other applicable therapeutic guidance calculation, or for the creation of an alarm signal, for instance to remind the user of taking the next dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys) 6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa http://en.wikipedia.org/wiki/Dalton_%28unit%29) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The mechanical arrangement of one embodiment of a supplemental device 2 and the manner in which it is attached to an injection device 1 will now be described with reference to FIGS. 8 to 14.

Figure 8:
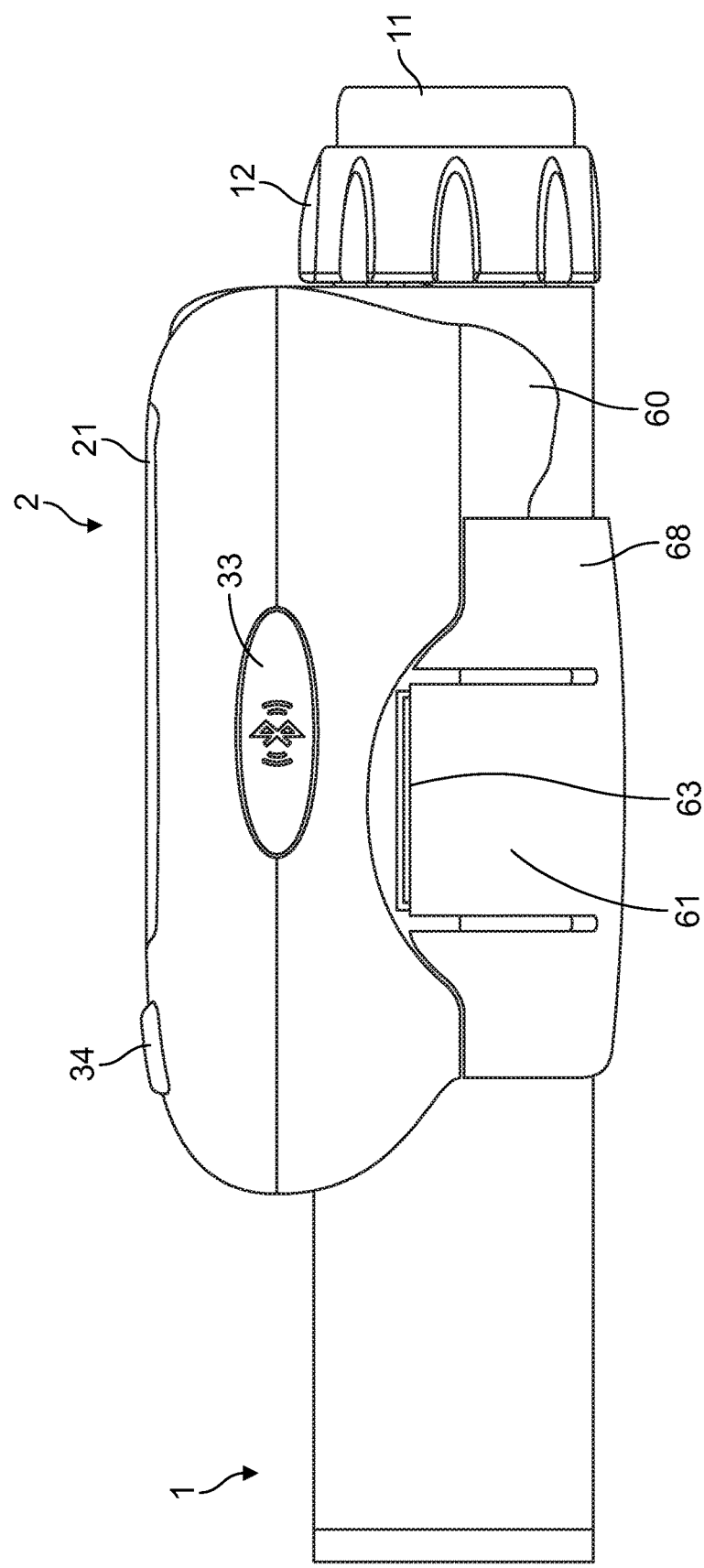

As is best seen from FIG. 8, the supplemental device 2 is attached to the injection pen 1 close to the dosage knob 12 with the display 21 uppermost in the orientation shown (which is the same for all of FIGS. 8 to 14). The plane of the display 21 lies generally transverse to the longitudinal axis of the injection device 1, and is perpendicular to the page of FIGS. 8, 9, 10, 12, 13 and 14.

A closure 68 extends from a shaft 59 of a hinge, the closure extending underneath the injection pen. The closure 68 is connected to the supplemental device 2 on the right side (looking at the injection device 1 with the injection button closest to the viewer), extends underneath the injection pen 1 and connects with the supplemental device on the left side thereof The supplemental device 2 of these illustrated embodiments includes two features that contribute to correct alignment of the supplemental device 2 on the injection device 1, and one feature that results in securing of the supplemental device 2 to the injection device 1. The features that contribute to correct alignment of the supplemental device 2 on the injection device 1 can be termed alignment arrangements. The features that contribute to securing of the supplemental device 2 to the injection device 1 can be termed a securing arrangement.

The correct alignment of the supplemental device 2 on the injection device 1, ensures that the OCR reader 25 is correctly aligned with the dosage window 13. Correct alignment allows correct operation and reliable readings. Ensuring that there can be correct alignment between the supplemental device 2 and the injection device 1 in use allows a simpler design for the OCR reader 25, in particular because it does not need to be designed to be able to accommodate different alignments between the devices 1, 2.

The first alignment feature is a locating channel 71. The locating channel 71 is located at the uppermost part of an injection device receiving channel 58 that is defined between the main body of the supplemental part and the closure 68 when in the closed position.

Figure 11A:
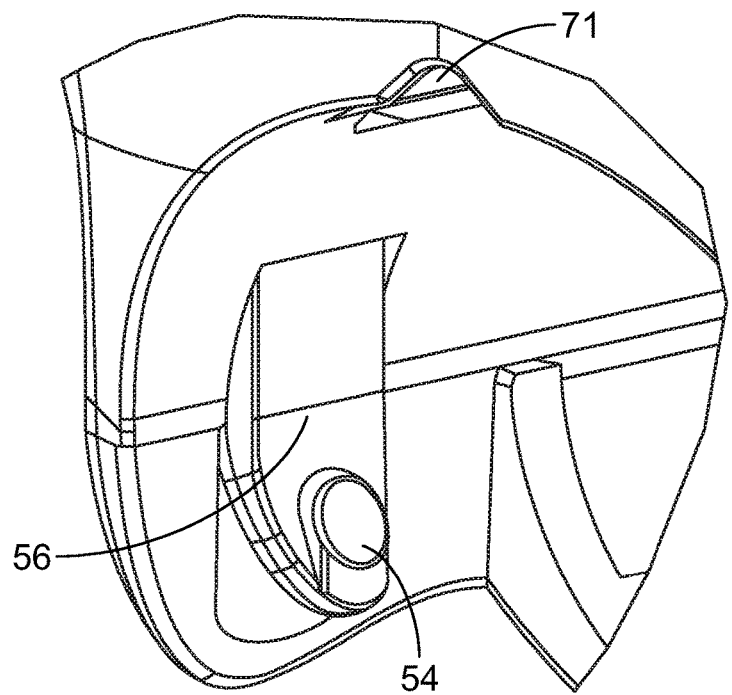
FIG. 11a is a partial cutaway perspective view of a detail from FIG. 10.
Figure 11B:
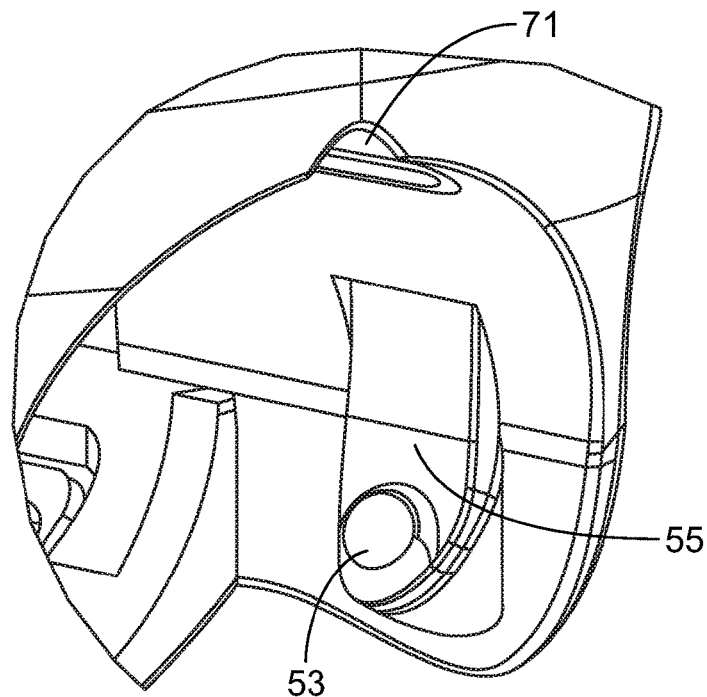
FIG. 11b is a partial cutaway perspective view of another detail from FIG. 10.

The locating channel 71 is best shown in FIGS. 11a and 11b. From here, it will be seen that the locating channel is formed at the end of the supplemental device that is closest to the dosage knob 12 when the supplemental device 2 is fitted to the injection device 1.

As is best seen in FIG. 1b, the locating rib 70 is located between the display window 13 and the dosage knob 12. In this example, the locating rib 70 extends for the whole of the distance between the display window 13 and the dosage knob 12. In other examples, the locating rib is shorter. The locating rib 70 is taller at the end that is adjacent the dosage knob 12 and tapers down to a zero height at the junction with the display window 13. As can be seen from FIG. 1b, the taper of the uppermost edge of the locating rib 70 is slightly curved. The gradient of the taper is less at the part of the locating rib 70 that is closest to the dosage knob 12 and is greater along the locating rib to the location of the display window 13. The shape of the locating rib 70 is such that the gradient continually increases as one moves from the position of the locating rib 70 that is adjacent to the dosage knob 12 to the position of the locating rib 70 that is adjacent the display window 13.

The thickness of the locating rib 70, the thickness being the dimension that is circumferential to the main body of the injection device 1, varies along the length of the locating rib 70. The thickness of the locating rib 70 is greatest at the end adjacent the dosage knob 12 and is least at the end adjacent the display window 13. The thickness of the locating rib 70 gradually decreases as one moves from the end of the locating rib adjacent the dosage knob 12 to the end of the locating rib that is adjacent the display window 13.

The cross-section of the locating rib, the cross-section being a section taken perpendicular to the longitudinal axis of the injection pen 1, is of a rounded triangle. The cross-section of the locating rib 70 is approximately the same for its entire length, although of course the size varies.

The locating channel 71 is dimensioned so as to correspond closely to the shape and size of the locating rib 70 that is present on the injection pen 1.

The locating channel 71 has a size and shape that corresponds closely to the size and shape of the locating rib 70. The locating channel 71 is slightly larger than the locating rib so as to ensure that the locating rib can be located within the locating channel 71. When the locating rib 70 is within the locating channel 71, the corresponding sizes ensure that the two features mate together. This assists in ensuring correct positioning of the supplemental device 2 on the injection device 1.

Figure 12:
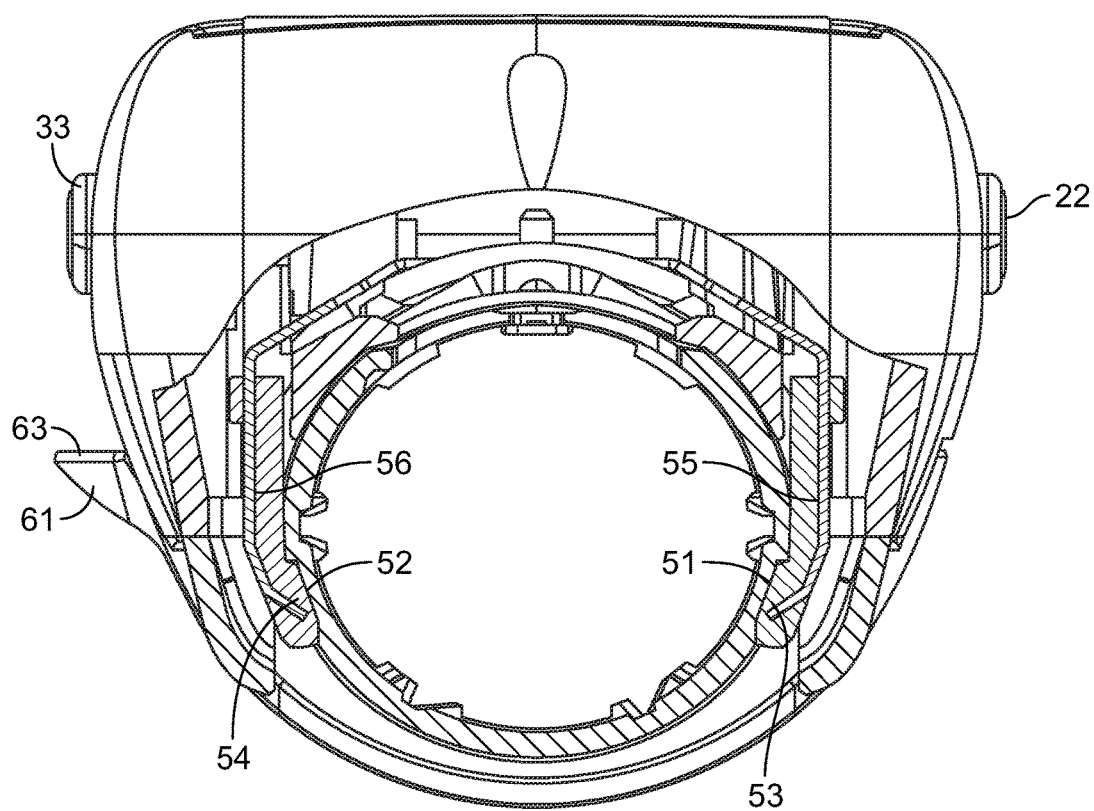
FIG. 12 is a cross-sectional view which is the same as FIG. 10 although with the supplemental device mated to the injection device.

Other features of the supplemental device 2 and the injection pen 1 that assist in ensuring correct alignment between the two devices will now be described. As best seen in FIG. 1b, the injection pen 1 is provided with indents on either side of its body at locations close to the dosage knob 12. In FIG. 1b, a left side indent 52 is shown. A right indent 51, which is shown in FIGS. 10 and 12, is located in a corresponding position on the right side of the injection pen 1.

The left and right indents 51, 52 are relatively shallow depressions. The indents 51, 52 have sloping sides, that is the sides of the indents 51, 52 are not parallel. Also, they are not radial with respect to the longitudinal axis of the injection pen 1. In these embodiments, the slope of the sides of the left and right indents 51, 52 is different for different parts of the indents. In particular, the gradient of the slope of the sides of the indents is less at the part of the indents that is furthest from the display window 13 and is greatest at the part of the indents 51, 52 that is closest to the display window 13. In these examples, the slope of the indents changes between these two extremes, for instance in a linear fashion.

The slope of the sides of the indent may for instance be between 30 and 70 degrees at the part that is furthest from the display window 13. The slope may for instance be between 60 and 80 degrees for the part that is closest to the display window 13. The greater angle of slope at the part closer to the display window 13 aids engagement of a face of a protuberance within the indent 51, 52 in such a way as to provide some resistance against removal of the supplemental device 2 in a direction radial to the longitudinal axis of the injection device 1.

Figure 10:
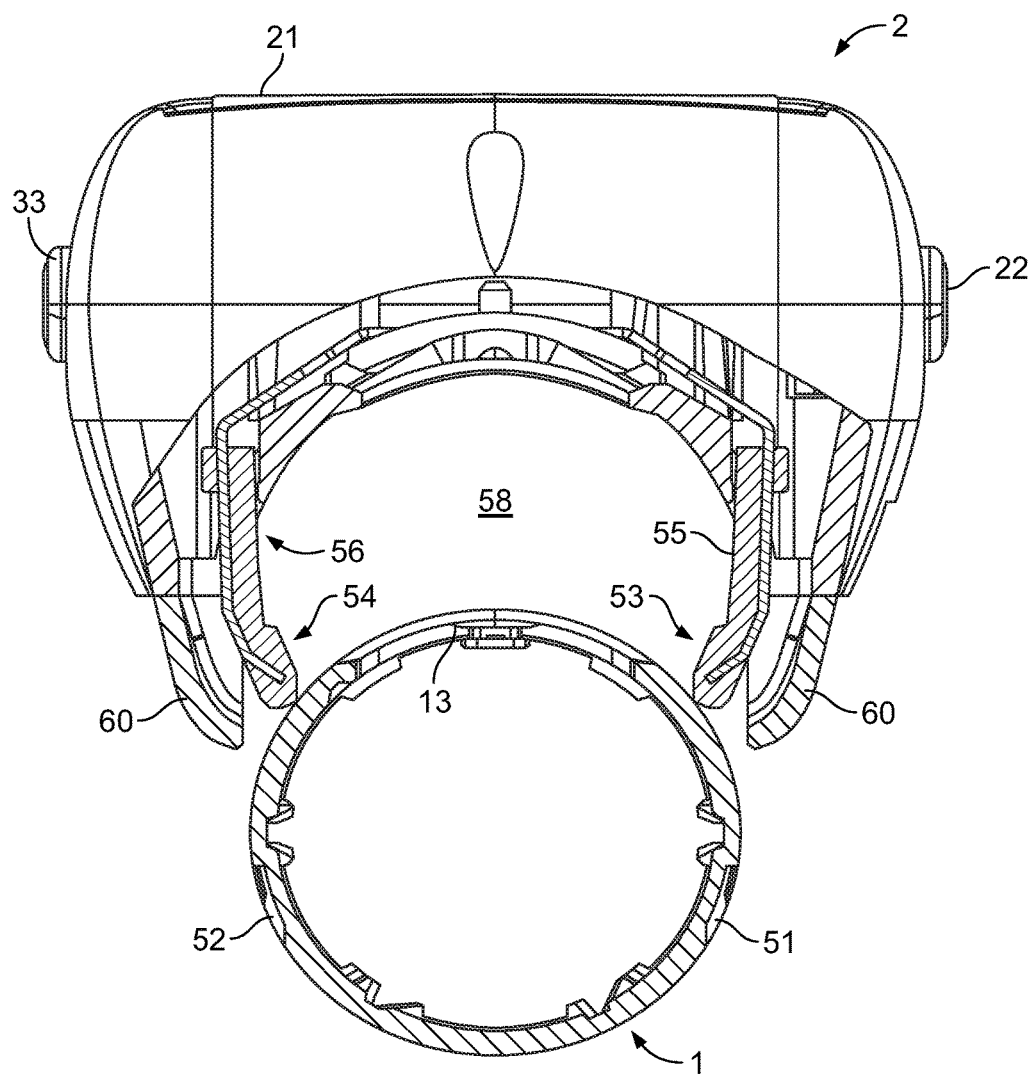
FIG. 10 is a cross-section view through the arrangement of the supplemental device and the injection pen of FIG. 8 prior to engagement of the supplemental device on the injection device.

As is best seen in FIGS. 10 and 11, the left and right protuberances 53, 54 are shaped to correspond to the shapes of the right and left indents 51, 52 respectively. In this way, the right and left protuberances 53, 54 fit within the right and left indents 51, 52 respectively when the supplementary device 2 is correctly positioned on the injection pen 1. The external dimensions of the right and left protuberances 53, 54 are slightly smaller than the internal dimensions of the right and left indents 51, 52 so as to ensure that the protuberances fit within their respective indent.

In these embodiments, the left and right protuberance 52 is shaped to correspond closely to the shape of the right indent 51. In this way, the right protuberances 53 fits snugly within the right indent 51 when the supplementary device 2 is correctly positioned on the injection pen 1. The left protuberance 54 is shaped similarly to the right protuberance 53, although it is less tall. Put another way, it is like the right protuberance 53 but with the top part missing or cut off. This is the reason for the end face of the left protuberance 54 having a larger area than the right protuberance 53. The different sizes for the protuberances 53, 54 helps the protuberances find engagement within the indents 51, 52. The right protuberance 53 can be consider to be a master to the left protuberance, which is a slave.

The right protuberance 53 is located at the end of the right arm 55, which is best shown in FIG. 11b.

As can be seen from FIG. 11a, the left protuberance 54 is located at the end of the left arm 56.

As can be best seen from FIG. 10, the right and left arms 55, 56 depend substantially vertically from the body 20 of the supplementary device 2. The right and left arms 55, 56 are thus formed either side of the injection device receiving channel 58.

A biasing feature 67, in the form of a u-shaped spring, is coupled to each of the right and left arms 55, 56. The effect of the spring 67 is to bias the right and left arms into a certain position. The position into which the right and left arms 55, 56 are biased is such that the distance between the innermost surfaces of the right and left protuberances 53, 54 is slightly less than the distance between the bottoms of the right and left indents 51, 52. The effect of the spring 67 is to resist movement of the protuberances 53, 54 and the arms 55, 56, away from one another.

Because the slopes of the sides of the protuberances 53, 54 match the sides of the indents 51, 52, the sloped sides of the protuberances 53, 54 at the distal ends of the arms 55, 56 is relatively shallow. This assists in sliding the protuberances 53, 54 over the external surface of the body 10 of the injection pen 1 as the supplemental device is being fitted. This is best demonstrated with reference to FIGS. 10 and 12.

As is shown in FIG. 10, the supplemental device 2 is located with respect to the injection pen 1 such that the ends of the right and left arms 55, 56, in particular the protuberances 53, 54, are just touching the housing 10 of the injection pen 1. The protuberances 53, 54 here contact the housing to the left and right sides of the display window 13.

The left and right arms 55, 56 are present behind flaps 60 that depend from the supplemental device 2 on both the left and right sides. As can be seen from FIG. 10, the flaps, or protecting walls 60, extend slightly further in a downwards direction than the arms. The flaps 60 are formed of transparent material. This allows a user to be able to view the locations of the arms 55, 56 relative to the indents 51, 52, which may help them to locate the supplemental device 2 correctly on the injection device 1. FIG. 8 shows the location of the left indent 52 in dotted form, to highlight the location of the arms, 55, 56 as well as the indents 51, 52, although the arms are not shown in this view.

In order to mate the supplemental device 2 with the injection device 1, the user first arranges the supplemental device 2 with respect to the injection device 1 as shown in FIG. 10, and then applies a force downwards on the supplemental device 2 while at the same time applying a force upwards on the injection device 1. This places force on the protuberances 53, 54, and thus the right and left arms 55, 56. As the injection device 1 and the supplemental device 2 move closer together, the force results in the arms being moved apart, against the resilience of the spring 67. This causes the spring 67 to apply a reaction force, which resists entry of the injection device 1 into the injection device receiving channel 58. However, when the protuberances 53, 54 reach the location on the injection pen 1 at which they are directly in line with the longitudinal axis of the injection device 1, the reaction force supplied by the spring 67 ceases to increase upon further movement of the injection device 1 and the supplemental device 2 together. After this point, the movement of the injection pen 1 into the injection device receiving channel 58 is aided by the resilience of the spring 67.

After some further movement, the protuberances 53, 54 become aligned with the left and right indent 51, 52 and, due to the resilience of the spring 67, become engaged with the indents. Engagement provides haptic and audio feedback as the protuberances 53, 54 click or snap into the indents 51, 52. The feedback is enhanced by the force provided by the resilience of the spring 67. Once the protuberances 53, 54 are mated with the indents 51, 52, there is significant resistance to further movement of the supplemental device 2 relative to the injection device 1, due in part to the corresponding shapes of the protuberances 53, 54 and the indents 51, 52 and due in part to the biasing together of the arms 55, 56 by the spring 67.

If when the supplemental device 2 and the injection device 1 are moved together one of the indents 51, 52 is higher than the other, one of the protuberances 53, 54 will engage with the higher one of the indents before the other one of the protuberances reaches the other indent. In this case, the protuberance and indent that first meet become engaged, and present significant resistance to further movement of that protuberance relative to that indent. In this case, the tendency is naturally for the injection device 1 to be rotated relative to the supplemental device such that the other indent meets the other protuberance. Once the other indent meets the other protuberance, they mate together and considerable resistance is presented against further movement of the injection pen 1 relative to the supplemental device 2. In the scenario in which one of the protuberances meets an indent before the other protuberance meets its respective indent, the experience of the user is such that the injection pen 1 and the supplemental device 2 seem to move together initially with little or no rotation. Haptic and audio feedback is then provided when the first protuberance meets the corresponding indent, and after this point the injection device 1 seems to roll into place within the injection device receiving channel 58 until the other protuberance is received in the other indent, at which point further haptic and audio feedback is provided to the user.

Once the protuberances 53, 54 are mated in the indent 51, 52, the injection device 1 is fully located within the injection device receiving channel 58 as shown in FIG. 12. Here, it will be seen that the outermost surface of the display window 13 is generally aligned with a lowermost surface of the upper part of the supplemental device 2. This supplemental device 2 is shaped such that the injection device 1 fits snugly within the injection device receiving channel 58 and there are multiple points or areas of contact between the exterior surface of the housing 10 of the injection device 1 and the lowermost surface of the supplemental device 2 when the supplemental device and the injection pen 1 are in this relative position. Even in the absence of the mating of the protuberances 53, 54 with the indents 51, 52 at this point, the user would notice that there is a natural tendency for the injection pen 1 to sit at this location within the supplemental device 2.

When the supplemental device 2 is located with respect to the injection pen 1 such that the right and left protuberances 53, 54 are located within the right and left indents 51, 52 respectively, the locating rib 70 is engaged within the locating channel 71. Correct alignment of the supplemental device 2 with respect to the injection device 1 is thus provided in two ways: firstly, by the location of the locating rib 70 within the locating channel 71 and secondly by the locating of the protuberances 53, 54 within the indents 51, 52.

In the event that the user places the supplemental device 2 onto the injection pen 1 at a location such that the supplemental device 2 is slightly at the right of the position shown in FIG. 8, the locating rib 70 does not fit within the locating channel 71. In this case, the supplemental device 2 is prevented from being located fully over the injection pen 1 by the locating rib 70 resting against a surface of the supplemental device 2 that is in some way distal from the correct location within the locating channel 71. However, in this position, the ends of the protuberances 53, 54 have passed the halfway point of the circumference of the housing 10 of the injection device 1 and thus the spring 67 results in the injection device 1 being biased towards the supplemental device 2 so as to be located within the injection device receiving channel 58. A user would know that the supplemental device 2 had not mated correctly with the injection pen 1 because they would not have received any haptic feedback from the mating of the protuberances 53, 54 with the indents 51, 52. They would also notice that the end of the supplemental device that is closest to the dosage knob 12 was separated from the injection pen 1 by a distance greater than the separation of the supplemental device 2 from the injection pen 1 at the end of the supplemental device 2 distal from the dosage knob 12. In this situation, the user can engage the supplemental device 2 and the injection pen 1 simply by exerting a force against the supplemental device 2 and the injection pen 1 such as to move the supplemental device 2 leftwards in the direction shown in FIG. 8. This can be achieved in a one-handed fashion or in a two-handed fashion. As the supplemental device 2 and the injection device 1 move relative to one another, the locating rib and the locating channel become more and more engaged. The spring force provided by the spring 67 may assist relative movement of the supplemental device 2 and the injection device 1 in this manner. As the locating rib 70 and the locating channel 71 become more engaged, the end of the supplemental device 2 that is closest to the dosage knob 12 moves down towards the injection device 1. This movement continues until the locating rib 70 is completely within the locating channel 71, at which point the right and left protuberances 53, 54 also engage with the right and left indents 51, 52 respectively. At this point, haptic feedback is provided by the mating of the protuberances 53, 54 with the indents 51, 52 and the user can determine that the supplemental device 2 and the injection device 1 are properly located with respect to one another.

If the user locates the supplemental device onto the injection pen 1 such that the supplemental device is to the left of the position shown in FIG. 8, mating between the supplemental device 2 and the injection pen 1 will not occur. In this case, the locating rib 70 will not prevent the supplemental device 2 from being located flat against the injection pen 1. A user, noticing this, will know that the supplemental device 2 is located too far from the dosage knob 12. The user can engage the supplemental device 2 with the injection pen 1 simply by moving the supplemental device 2 relative to the injection device 1 such as to move the supplemental device 2 rightwards in the direction shown in FIG. 8.

If the locating rib 70 is aligned with the locating channel 71 when the end of the locating rib 70 that is closest to the display window 13, the smallest end of the locating rib 70 will enter the mouth, being the large open end, of the locating channel 71. At this stage, the supplemental device still is located against the surface of the injection device 1, with the injection device 1 being fully located within the injection device receiving channel 58. Because of the action of the spring 67, the injection device 1 is biased into the injection device receiving channel 58 against the supplemental device 2 at this stage.

If the locating rib 70 and the locating channel 71 are not exactly aligned, the narrowest end of the locating rib 70 will engage with a side of the locating channel. Further relative movement of the supplemental device 2 and the injection device 1 in a longitudinal direction results in a reactive force being applied between the locating rib and a wall of the locating channel 71, biasing the supplemental device 2 and the injection device 1 towards being in full alignment. This occurs until the locating rib 70 is fully engaged within the locating channel 71, at which point the right and left protuberances 53, 54 also engage with the right and left indents 51, 52. At this point, the supplemental device 2 and the injection device 1 are fully engaged with one another.

The supplemental device 2 is provided with a closure 68, which has a primary function of clamping the supplemental device 2 to the injection pen 1 when the two devices are mated with one another.

Figure 13:
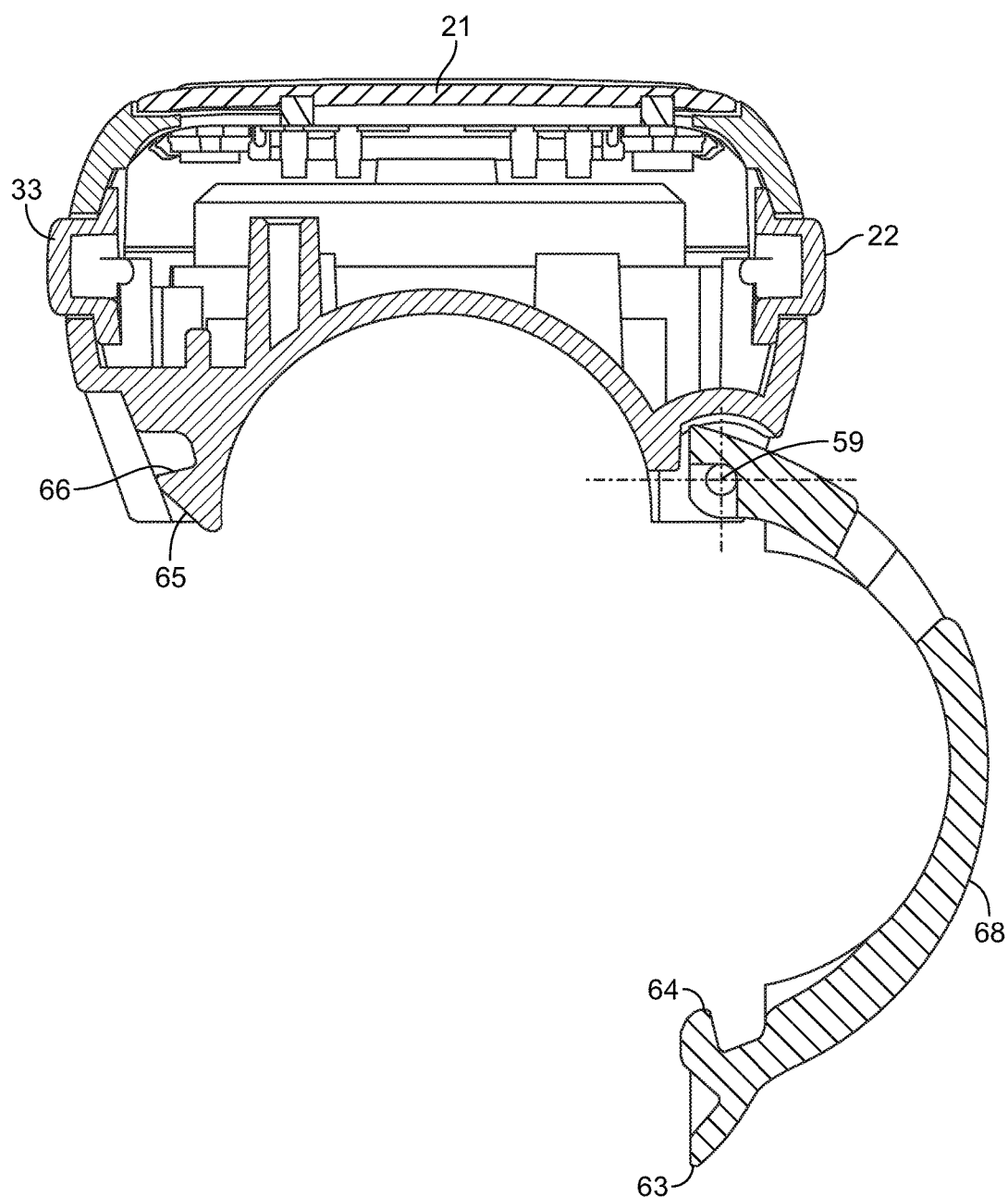
FIG. 13 is a cross-sectional view through the supplemental device of FIG. 2b at a location further along the device from the cross-section shown in FIG. 10.
Figure 14:
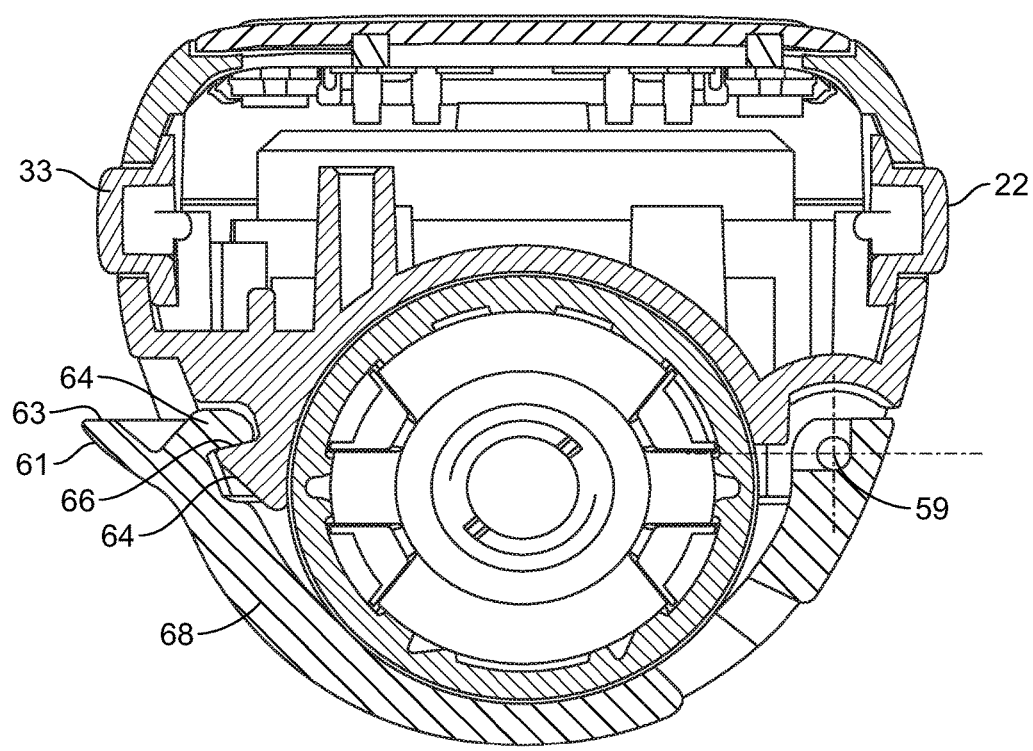
FIG. 14 is the same cross-section as shown in FIG. 13 although with the supplemental device installed on an injection pen and clamped in place.

As best seen in FIGS. 13 and 14, the closure 68 has an innermost surface that coincides with the curved surface of an imaginary cylinder. The diameter of the cylinder is the same as the external dimension of the housing 10 of the injection device 1. As such, the closure 68 forms a snug fit against the lowermost part of the housing 10 of the injection device 1 when the supplemental device 2 is in place on the injection device 1.

The closure 68 is moveable between an open position, shown in FIG. 13, and a closed position, shown in FIG. 14.

As can be seen in FIG. 8, the closure 68 is located next to the arm protecting walls 60, in a direction opposite the arm protecting walls 60 to the dosage knob 12. The closure 68 has a dimension in a longitudinal axis of the injection pen 1 that is approximately 60% of the length dimension of the supplemental device 2. In other examples, the length of the closure 68 in a longitudinal direction of the injection pen 1 may take a value anywhere between 30 and 80% of the length of the supplemental device 2, and preferably between 40 and 70% of the length of the supplemental device 2.

The material of the closure 68 has a generally uniform thickness. As such, the external surface of the closure 68, that is the surface that is furthest from the longitudinal axis of the injection pen 1 when the supplemental device 2 is mated with the injection pen 1, is generally cylindrical, or at least takes the form of part of a cylinder.

Figure 9:
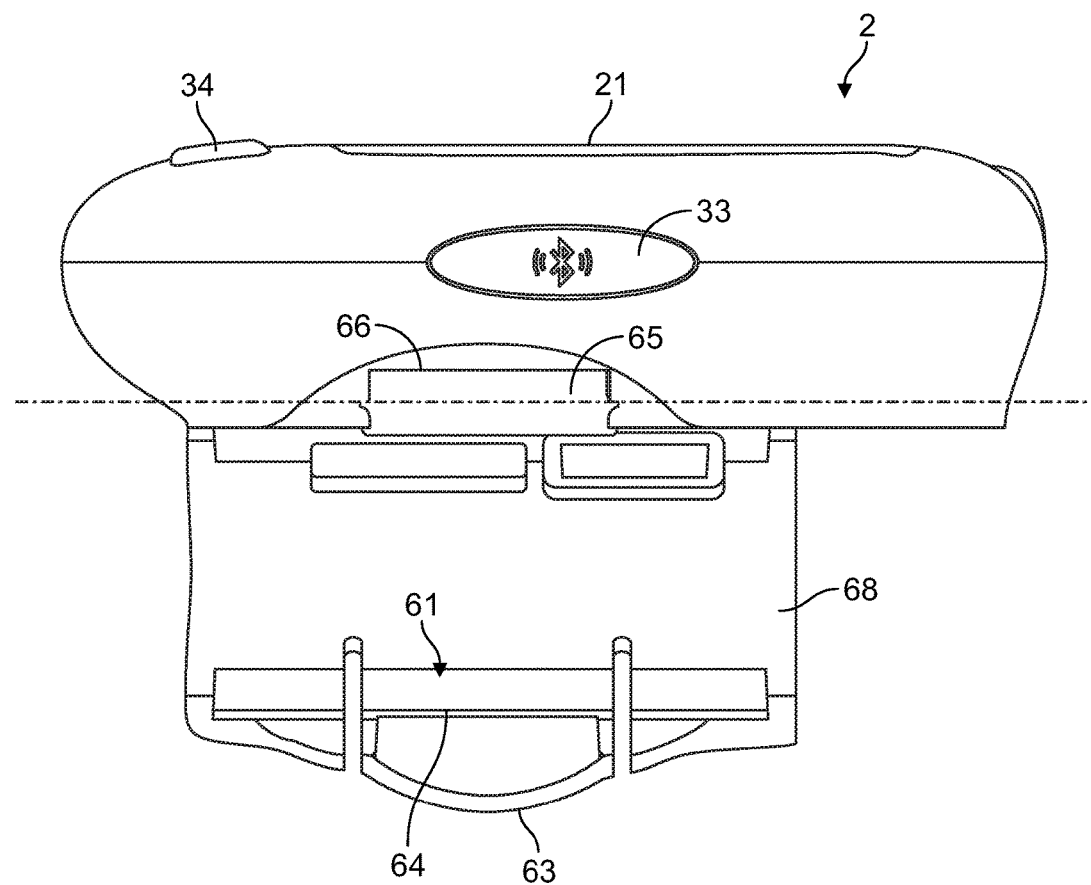
FIG. 9 (shown on two sheets FIG. 9a and FIG. 9b) is a side view of the supplemental device in the same view as FIG. 8 although with the injection pen omitted and with a closure open.

The closure 68 is provided with two cutaways 72, 73. The cutaways 72, 73 extend from an edge of the closure 68 that is furthest from the shaft 59 of the hinge formed at the other side of the supplemental device 2. The cutaways 72, 73 extend from this edge in a direction that is generally circumferential with respect to the injection pen 1. The length of the cutaways is approximately equal to 1/6 or 1/5 of the circumference of the circle on which the closure 68 generally lies. The cutaways 72, 73 define a tab 61. The tab 61 is connected to the main part of the closure 68 at a location between the lowermost ends of the cutaways 72, 73. A free end 63 of the tab 61 is located between the uppermost ends of the cutaways 72, 73. As is best seen in FIG. 9, the free end 63 of the tab 61 is curved so as to extend away from the longitudinal axis of the injection pen 1 by a greater extent at a point that is central between the cutaways 72, 73. This allows a user better to be able to locate a digit on the free end 63 of the tab 61 so as to be able to pull the free end 63 in a direction that is downwards and leftwards in FIG. 14.

On the inside surface of the tab 61 is provided a latching edge 64, which is best seen in FIGS. 9, 13 and 14. The latching edge 64 is provided at a junction between a latching face and another face. The latching edge 64 extends for the width of the tab 61. The latching face is in a plane that extends approximately radially with respect to the longitudinal axis of the injection 1 when the closure 68 is in the closed position, as shown in FIG. 14. In this position, the latching edge 64 is engaged with a latch engaging face 66 that is provided as a part of the uppermost portion of the supplemental device 2, i.e. is provided as a portion of the supplemental device 2 that is not part of the closure 68. The latch engaging face 66 is provided in a plane that is generally the same orientation as the plane of the latching face when the closure 68 is in the closed position.

When the user has mated the supplemental device 2 onto the injection pen 1, in particular mating the locating rib 70 within the locating channel 71 and locating the protuberances 53, 54 within the indents 51, 52, the user may secure the supplemental device 2 to the injection pen 1. This is achieved by the user moving the closure 68 from the position shown in FIG. 9, in which the injection device receiving channel 58 is open for inclusion of the injection pen 1 therein, and rotating the closure 68 around the shaft 59 of the hinge so as to move the free end 63 of the tab 61 towards the latch engaging face. Movement continues until contact is made between the innermost part of the latching edge 64 against a guide surface 65, which is located just beneath (as shown in the Figures) the latch engaging face 66. The guide surface 65 is angled approximately tangentially to the outside surface of the housing 10 of the injection pen 1.

At this point, the tendency of the closure 68 to adopt the shape shown in FIG. 13 provides a spring force between the end of the tab 61 and the guide surface 65. As the user exerts further force against the closure 68, the closure 68 deforms resiliently so as to increase the separation between the free end 63 of the tab 61 and the hinge 59. This allows the edge of the latching edge 64 to slide over the guide surface 65. This continues until the latching edge 64 becomes aligned with the edge between the guide surface 65 and the latch engaging face 66, at which point the latching edge 64 and the latching face engage within the channel that is formed against the latch engaging face 66. At this point, the resilience of the closure 68 results in the latching edge 64 and the latch engaging face 66 becoming engaged with one another, and at this point the components are in the position shown in FIG. 14. In this position, it will be seen that the innermost surface of the closure 68 is snug against the outermost surface of the housing 10 of the injection pen 1. At this point, the closure 68 ensures that the injection pen 1 is tightly contained within the injection device receiving channel 58 and is held in place by the closure 68.

It will be appreciated that this arrangement prevents movement of the injection device 1 relative to the supplemental device 2 in the plane of FIG. 14.

Movement of the supplemental device 2 along the longitudinal axis of the injection pen 1 is inhibited by the mating between the protuberances 53, 54 and the indents 51, 52. Additionally, movement of the supplemental device 2 in a rightwards direction as shown in FIG. 8 is further prevented by the locating rib 70 acting against the body 20 of the supplemental device 2.

Additionally, in some embodiments the supplemental device 2 is provided with one or more surfaces that are specifically configured to oppose sliding of the supplemental device 2 on the exterior surface of the housing 10 of the injection device 1. In particular, surfaces of the supplemental device 2 that contact the injection device 1 when the supplemental device 2 is engaged with the injection device 1 as shown in FIG. 8 may be provided with a high friction coating or may be formed of a high friction material. Such materials include rubberised materials, silicone, materials with roughened surfaces, materials which have some adhesive properties, and such like. Such surfaces may include one or more of an innermost surface of the closure 68, and/or a lowermost surface of the upper part of the supplementary device. These surfaces may extend for the whole of the surface of the supplementary device 2 that contacts the housing 10 of the injection device 1 during use, or may extend over only a part of the relevant surfaces.

In order to remove the supplemental device 2 from the injection pen 1, the user first places a digit, for instance a finger or thumb, on the uppermost surface of the free end 63 of the tab 61. The user then can exert a force downwards and leftwards as shown in FIG. 14. When the force applied is sufficient, the closure 68 will deform to a point where the latching edge 64 is no longer engaged with the latch engaging face 66. At this point, the closure 68 can be moved downwards, pivoting around the shaft 59 of the hinge. Indeed, if the injection device 1 is held at the orientation shown in FIG. 14, then gravity will assist the movement of the closure 68 in this direction. Once the closure 68 has been pivoted away from the injection device 1, the supplemental device 2 is no longer clamped to the injection device 1. In this position, the supplemental device 2 is held onto the injection device 1 only by the mating of the protuberances 53, 54 and the indents 51, 52.

In order to remove the supplemental device 2 completely, the user may grasp the supplemental device 2 in one hand and apply a force to it in a direction upwards as shown in FIG. 8. Once the force applied is sufficient to overcome the spring and friction forces, the sloping surface of the indents 51 and 52 that are uppermost in FIG. 10 slide over the corresponding sloping surfaces of the protuberances 53, 54. As this occurs, the left and right arms 55, 56 are moved apart, against the bias of the spring 67. Once the protuberances 53, 54 are free of the indents 51, 52, the user experiences relatively little resistance as the supplemental device 2 is removed from the injection pen 1. Of course, the cooperation between the locating rib 70 and the locating channel 71 does not present any obstacle to separating the supplemental device 2 and the injection pen 1 in this way.

Alternatively, the user may grasp the supplemental device and move it in a direction that is rightwards in FIG. 8. In this case, the locating rib and the locating channel 71 cooperate to assist in removal of the protuberances from the indents 51, 52. In particular, as the supplemental device 2 begins to move slightly with respect to the injection device 1 in the rightwards direction, the locating rib 70 slides deeper into the locating channel, which results in an upwards force being applied to the supplemental device 2 relative to the injection pen 1. This upwards force then assists in overcoming the spring and friction forces needed to remove the protuberances 53, 54 from the indents 51, 52.

As can be seen in FIGS. 11a and 11b, the left and right arms 55, 56 are restrained on either side by the main body of the supplemental device 2. This can prevent or inhibit movement of the left and right arms 55, 56 in a direction that is perpendicular to the page of FIG. 10. This assists in maintaining the supplemental device 2 in the correct location after installation on the injection pen 1 even in the presence of (low) forces acting to move the supplemental device 2 along the longitudinal axis of the injection pen 1. The arms 55, 56 can be termed support members because they support the protuberances.

In some embodiments, the left and right arms 55, 56 are free to move slightly in a direction that is perpendicular to the page of FIG. 10. In these embodiments, the body 20 of the supplemental device 2 can move relative to the housing 10 of the injection pen 1 whilst the protuberances 53, 54 remain fully engaged within the indents 51, 52. This prevents the engagement between the protuberances 53, 54 and the indents 51, 52 significantly restricting movement of the supplemental device 2 in the rightwards direction shown in FIG. 8, at least until the interaction between the locating rib 70 and the locating channel 71 causes the supplemental device 2 to be moved upwards relative to the injection pen 1.

In some other embodiments, the left and right arms 55, 56 are configured such that they are significantly resistant to movement in a direction that is perpendicular to the page of FIG. 10. In these embodiments, the arms 55, 56 may include a triangular structure with the protuberance at one corner and fixings to the main body of the supplemental device 2 at the other two corners. These two other corners may be separated in the axial length of the supplemental device 2. The triangular structure may comprise three limbs or it may be sheet-like. It may be planar or it may be curved.

In some embodiments, the locating rib 70 and the locating channel 71 are absent. In these embodiments, the correct alignment between the supplemental device 2 and the injection pen 1 is provided by mating of the protuberances 53, 54 and the indents 51, 52.

In some other embodiments, the right and left arms 55, 56 and the protuberances 53, 54 are absent. In these embodiments, the correct alignment between the supplemental device 2 and the injection device 1 is provided by the locating rib 70 and the locating channel 71.

Of course, other alternative arrangements for ensuring a correct relative position between the supplemental device 2 and the injection pen 1 will be envisaged by the skilled person, and all such alternatives are within the scope of the invention except when explicitly excluded by the language of the claims.

Also, the skilled person will be aware of alternative securing arrangements, for instance clamping, the supplemental device 2 to the injection pen 1 once the correct relative position has been attained. All such alternatives are within the scope of this invention unless they are precluded by the language of the claims. Such alternatives include various other latching mechanisms involving a resilient component, such as a tab or an arm, and no complicated moving parts. Other such embodiments involve more complicated moving parts, for instance clamps with twist-to-lock mechanisms, tension clips and other such mechanisms. A hinge is a relatively simple way of connecting the main body of a supplemental device with a closure part, although alternative connection arrangements will be envisaged by the skilled person. Suitable connection arrangements may include slide mechanisms, clips, etc.

The invention claimed is:

1. A supplemental device for attachment to an injection device, the supplemental device comprising:
   an aligning arrangement for ensuring a predetermined positional relationship between the supplemental device and the injection device; and
   a securing arrangement for securing the supplemental device to the injection device,
   wherein the supplemental device has a main body defining an injection device receiving channel, and
   wherein the securing arrangement comprises a closure that is removably attachable across the injection device receiving channel.

2. A supplemental device as claimed in claim 1, wherein the aligning arrangement and the securing arrangement are separate arrangements.

3. A supplemental device as claimed in claim 1, wherein the aligning arrangement comprises a locating channel in a main body of the supplemental device, the locating channel being configured to mate with a locating rib on the injection device.

4. A supplemental device as claimed in claim 3, wherein the locating channel is located at one end of the main body of the supplemental device.

5. A supplemental device as claimed in claim 1, wherein the aligning arrangement comprises first and second protuberances located on first and second support members respectively, the supplemental device being configured such that the protuberances engage in indents on the injection device when the predetermined positional relationship is present.

6. A supplemental device as claimed in claim 5, wherein the supplemental device has a main body defining an injection device receiving channel, wherein the protuberances are located one either side of the injection device receiving channel, and wherein the support members are biased towards each other.

7. A supplemental device as claimed in claim 6, wherein the protuberances have sloping sides, and wherein a gradient of a side of each protuberance that is closest to the bottom of the injection device receiving channel is greater than a gradient of a side of the protuberance that is furthest from the bottom of the injection device receiving channel.

8. A supplemental device as claimed in claim 1, wherein the supplemental device includes an optical reading arrangement and wherein the optical reading arrangement is directed at and at least partially covers a display of the injection device when the predetermined positional relationship between the supplemental device and the injection device is present.

9. A supplemental device as claimed in claim 1, wherein the securing arrangement is movably attached to the main body at a first side of the injection device receiving channel.

10. A supplemental device as claimed in claim 1, wherein the securing arrangement is hinged to the main body at a first side of the injection device receiving channel.

11. A supplemental device as claimed in claim 1, wherein the securing arrangement is removably connectable to the main body of the supplemental device at a second side of the injection device receiving channel by a latch and catch arrangement.

* * * * *